(12) United States Patent
Huth et al.

(10) Patent No.: US 7,148,357 B2
(45) Date of Patent: Dec. 12, 2006

(54) VEGFR-2 AND VEGFR-3 INHIBITORY ANTHRANILAMIDE PYRIDINES

(75) Inventors: Andreas Huth, Berlin (DE); Ludwig Zorn, Berlin (DE); Martin Kruger, Berlin (DE); Stuat Ince, Berlin (DE); Karl-Heinz Thierauch, Berlin (DE); Andreas Menrad, Berlin (DE); Martin Haberey, Berlin (DE); Holger Hess-Stumpp, Berlin (DE)

(73) Assignee: Schering AG, Berlin (DE)

( * ) Notice: Subject to any disclaimer, the term of this patent is extended or adjusted under 35 U.S.C. 154(b) by 258 days.

(21) Appl. No.: 10/631,018

(22) Filed: Jul. 31, 2003

(65) Prior Publication Data

US 2004/0147535 A1  Jul. 29, 2004

Related U.S. Application Data

(60) Provisional application No. 60/483,896, filed on Jul. 2, 2003, provisional application No. 60/407,970, filed on Sep. 5, 2002.

(30) Foreign Application Priority Data

Jul. 31, 2002 (DE) ................................ 102 35 690
Jun. 19, 2003 (DE) ................................ 103 28 036

(51) Int. Cl.
*C07D 401/10* (2006.01)

(52) U.S. Cl. .................................................. 546/275.7

(58) Field of Classification Search .............. 546/275.7
See application file for complete search history.

(56) References Cited

U.S. PATENT DOCUMENTS

2002/0147198 A1* 10/2002 Chen et al. ................. 514/247

* cited by examiner

*Primary Examiner*—Patricia L. Morris

(57) ABSTRACT

VEGFR-2 and VEGFR-3 inhibitory anthranilamide pyridinamides, their production and use as pharmaceutical agents for treating diseases that are triggered by persistent angiogenesis, as well as intermediate products for the production of the compounds are described. The compounds according to the invention can be used as or in the case of tumor or metastasis growth, psoriasis, Kaposi's sarcoma, restenosis, such as, e.g., stent-induced restenosis, endometriosis, Crohn's disease, Hodgkin's disease, leukemia; arthritis, such as rheumatoid arthritis, hemangioma, angiofibroma; eye diseases, such as diabetic retinopathy, neovascular glaucoma; renal diseases, such as glomerulonephritis, diabetic nephropathy, malignant nephrosclerosis, thrombic microangiopathic syndrome, transplant rejections and glomerulopathy; fibrotic diseases, such as cirrhosis of the liver, mesangial cell proliferative diseases, arteriosclerosis, injuries to nerve tissue, and inhibition of the reocclusion of vessels after balloon catheter treatment, in vascular prosthetics or after mechanical devices are used to keep vessels open, such as, e.g., stents, as immunosuppressive agents, as a support in scar-free healing, senile keratosis and contact dermatitis. The compounds according to the invention can also be used as VEGFR-3 inhibitors in the case of lymphangiogenesis.

3 Claims, No Drawings

VEGFR-2 AND VEGFR-3 INHIBITORY ANTHRANILAMIDE PYRIDINES

This application claims benefit of U.S. Provisional Application No. 60/407,970 filed on Sep. 5, 2002 and U.S. Provisional Application No. 60/483,896, filed on Jul. 2, 2003.

The invention relates to VEGFR-2 and VEGFR-3 inhibitory anthranilamide pyridines, their production and use as pharmaceutical agents for treating diseases that are triggered by persistent angiogenesis as well as intermediate products for the production of compounds.

Persistent angiogenesis can be the cause or precondition of various diseases, such as tumor or metastasis growth, psoriasis; arthritis, such as rheumatoid arthritis, hemangioma, angiofibroma; eye diseases, such as diabetic retinopathy, neovascular glaucoma; renal diseases, such as glomerulonephritis, diabetic nephropathy, malignant nephrosclerosis, thrombic microangiopathic syndrome, transplant rejections and glomerulopathy; fibrotic diseases, such as cirrhosis of the liver, mesangial cell proliferative diseases and arteriosclerosis, or can result in an aggravation of these diseases.

Persistent angiogenesis is induced by the factor VEGF via its receptor. So that VEGF can exert this action, it is necessary that VEGF bind to the receptor, and a tyrosine phosphorylation is induced.

Direct or indirect inhibition of the VEGF receptor (VEGF=vascular endothelial growth factor) can be used for treating such diseases and other VEGF-induced pathological angiogenesis and vascular permeable conditions, such as tumor vascularization. For example, it is known that the growth of tumors can be inhibited by soluble receptors and antibodies against VEGF.

Anthranilamide pyridones that are used as pharmaceutical agents for treating psoriasis; arthritis, such as rheumatoid arthritis, hemangioma, angiofibroma; eye diseases, such as diabetic retinopathy, neovascular glaucoma; renal diseases, such as glomerulonephritis, diabetic nephropathy, malignant nephrosclerosis, thrombic microangiopathic syndrome, transplant rejections and glomerulopathy; fibrotic diseases, such as cirrhosis of the liver, mesangial cell proliferative diseases, arteriosclerosis, injuries to nerve tissue, and for inhibiting the reocclusion of vessels after balloon catheter treatment, in vascular prosthetics or after mechanical devices are used to keep vessels open, such as, e.g., stents, are known from WO 00/27820 (e.g., Example 38).

The compounds that are known from WO 00/27820 are generally effective in the indications cited, but their effectiveness is not very pronounced.

Anthranilic acid amides that are are highly effective but also have a good inhibition of the Cytochrome P 450 isoenzyme 3A4 are also known from WO 00/27819 (Example 2.54). The Cytochrome P 450 isoenzyme 3A4 is one of the essential metabolic enzymes via which pharmaceutical agents are degraded. An inhibition of this isoenzyme results in undesirable pharmaceutical agent interactions, especially in the case of multimorbid patients (patients with multiple disease conditions). There also exists the problem that in a combination therapy with other medications, increased toxicity occurs, which results from the inhibition of the degradation of the compounds and the associated excessive serum levels.

There is therefore the desire for active ingredients that on the one hand are effective and on the other hand are more compatible or do not exhibit any undesirable side effects.

There is therefore a desire for, on the one hand, more effective, and, on the other hand, more compatible compounds.

It has now been found that compounds of general formula I

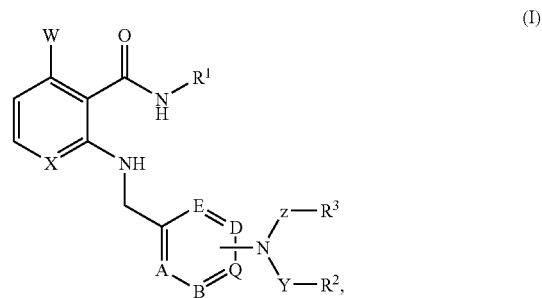

in which
X stands for CH or N,
W stands for hydrogen or fluorine,
A, B, D,
E and Q, in each case independently of one another, stand for a nitrogen or carbon atom, whereby only a maximum of two nitrogen atoms can be present in the ring,
$R^1$ stands for aryl or heteroaryl, which optionally can be substituted in one or more places in the same way or differently with halogen, hydroxy, $C_1$–$C_{12}$-alkyl, $C_3$–$C_6$-cycloalkyl, $C_3$–$C_6$-alkenyl, $C_2$–$C_6$-alkinyl, aralkyloxy, $C_1$–$C_{12}$-alkoxy, halo-$C_1$–$C_6$-alkyl, cyano-$C_1$–$C_6$-alkyl or with the group =O, —$SO_2R^6$ or —$OR^5$, whereby the $C_1$–$C_6$-alkyl optionally also can be substituted with the group —$OR^5$ or —$NR^9R^{10}$,
Y and Z, in each case independently of one another, stand for a bond or for the group =CO, =CS or =$SO_2$,
$R^2$ and $R^3$, independently of one another, stand for hydrogen or for the group —$CONR^9R^{10}$, —$SO^2R^6$, —$COR^{11}$, —$COC_1$–$C_6$-alkyl, —CO—$C_1$–$C_6$-alkyl-$R^{11}$, —$NR^9R^{10}$ or for $C_1$–$C_6$-alkyl, $C_3$–$C_{10}$-cycloalkyl, $C_3$–$C_6$-cycloalkenyl, aryl or heteroaryl that is optionally substituted in one or more places in the same way or differently with halogen, cyano, $C_1$–$C_{12}$-alkyl, $C_1$–$C_{12}$-alkoxy, hydroxy-$C_1$–$C_6$-alkyl, halo-$C_1$–$C_6$-alkyl or with the group —$NR^7R^8$, —$OR^5$, —$C_1$–$C_6$-alkyl-$OR^5$, —$SR^4$, —$SOR^4$ or —$SO_2R^6$, or
$R^2$, $R^3$, Y
and Z together with the nitrogen atom form a 3- to 8-membered saturated or unsaturated ring, which optionally can contain additional heteroatoms in the ring and optionally can be substituted in one or more places in the same way or differently with halogen, cyano, $C_1$–$C_{12}$-alkyl, $C_1$–$C_{12}$-alkoxy, halo-$C_1$–$C_6$-alkyl, hydroxy-$C_1$–$C_6$-alkyl, or with the group =O, —$OR^5$, —$SR^4$, —$SOR^4$ or —$SO_2R^6$,
$R^4$ stands for $C_1$–$C_{12}$-alkyl, aryl or heteroaryl,
$R^5$ stands for hydrogen, $C_1$–$C_{12}$-alkyl, $C_3$–$C_{10}$-cycloalkyl, $C_1$–$C_{12}$-alkoxy, halo-$C_1$–$C_{12}$-alkyl, or halo-$C_3$–$C_6$-cycloalkyl,
$R^6$ stands for hydrogen, $C_1$–$C_{12}$-alkyl, halo-$C_1$–$C_6$-alkyl, aryl or heteroaryl, or for the group —$NR^9R^{10}$, whereby the aryl or heteroaryl itself optionally can be substituted in one or more places in the same way or differently with $C_1$–$C_{12}$-alkyl, $C_1$–$C_6$-alkoxy, halogen or halo-$C_1$–$C_6$-alkoxy, $R^7$ and $R^8$, independently of one another, stand for hydrogen or $C_1$–$C_{12}$-alkyl, $R^9$ and $R^{10}$, independently of one another, stand for hydrogen, $C_1$–$C_6$-alkyl, $C_2$–$C_6$-alkenyl, aryl, $C_3$–$C_8$-cycloalkyl or for the group —CONR$^7$R$^8$, or for $C_1$–$C_{12}$-alkyl that is optionally substituted in one or more places in the same way or differently with aryl, morpholino, hydroxy, halogen, $C_1$–$C_{12}$-alkoxy, or with the group —NR$^7$R$^8$, whereby the aryl itself optionally can be substituted in one or more places in the same way or differently with $C_1$–$C_6$-alkoxy or halo-$C_1$–$C_6$-alkyl, or $R^9$ and $R^{10}$ together form a 5- to 8-membered ring that can contain additional heteroatoms, and $R^{11}$ stands for $C_1$–$C_6$-alkyl, $C_1$–$C_6$-alkoxy, hydroxy-$C_1$–$C_6$-alkyl, hydroxy-$C_1$–$C_6$-alkoxy, $C_3$–$C_6$-cycloalkyl, phenyl, pyridyl, biphenyl or naphthyl, whereby the phenyl itself can be substituted in one or more places in the same way or differently with $C_1$–$C_6$-alkyl, or halo-$C_1$–$C_6$-alkyl, as well as isomers, diastereomers, tautomers and salts thereof, exhibit improved properties, i.e., high effectiveness with simultaneously less CYP450 3A4 inhibition.

The compounds according to the invention prevent a tyrosine phosphorylation or stop persistent angiogenesis and thus the growth and propagation of tumors, whereby they are distinguished in particular by a slighter inhibition of isoforms of Cytochrome P 450 (3A4).

Medication using the compounds according to the invention can therefore also be done at no risk even without regard to pharmaceutical agents that are administered at the same time and that are degraded via these isoforms.

Alkyl is defined in each case as a straight-chain or branched alkyl radical, such as, for example, methyl, ethyl, propyl, isopropyl, butyl, isobutyl, sec-butyl, pentyl, isopentyl or hexyl, heptyl, octyl, nonyl, decyl, undecyl, or dodecyl.

Alkoxy is defined in each case as a straight-chain or branched alkoxy radical, such as, for example, methyloxy, ethyloxy, propyloxy, isopropyloxy, butyloxy, isobutyloxy, sec-butyloxy, pentyloxy, isopentyloxy, hexyloxy, heptyloxy, octyloxy, nonyloxy, decyloxy, undecyloxy or dodecyloxy.

Cycloalkyls are defined as monocyclic alkyl rings, such as cyclopropyl, cyclobutyl, cyclopentyl, cyclohexyl, or cycloheptyl, cyclooctyl, cyclononyl or cyclodecyl, but also bicyclic rings or tricyclic rings, such as, for example, adamantanyl.

Cycloalkyl radicals can contain, instead of the carbon atoms, one or more heteroatoms, such as oxygen, sulfur and/or nitrogen. Those heterocycloalkyls with 3 to 8 ring atoms are preferred.

Cycloalkenyl is defined in each case as cyclobutenyl, cyclopentenyl, cyclohexenyl, cycloheptenyl, cyclooctenyl, cyclononenyl or cyclodecenyl, whereby the linkage can be carried out both to the double bond and to the single bonds.

Halogen is defined in each case as fluorine, chlorine, bromine or iodine.

Halo-alkyl, halo-alkoxy, etc., is defined in that the alkyl, alkoxy, etc., is substituted in one or more places, in the same way or differently, with halogen.

Alkenyl is defined in each case as a straight-chain or branched alkenyl radical that contains 2–6, preferably 4–6, C atoms. For example, the following radicals can be mentioned: vinyl, propen-1-yl, propen-2-yl, but-1-en-1-yl, but-1-en-2-yl, but-2-en-1-yl, but-2-en-2-yl, 2-methyl-prop-2-en-1-yl, 2-methyl-prop-1-en-1-yl, but-1-en-3-yl, but-3-en-1-yl, and allyl.

The aryl radical in each case comprises 3–12 carbon atoms and can in each case be benzocondensed.

For example, there can be mentioned: cyclopropenyl, cyclopentadienyl, phenyl, tropyl, cyclooctadienyl, indenyl, naphthyl, azulenyl, biphenyl, fluorenyl, anthracenyl, etc.

The heteroaryl radical in each case comprises 3–16 ring atoms, and instead of the carbon can contain one or more heteroatoms that are the same or different, such as oxygen, nitrogen or sulfur, in the ring, and can be monocyclic, bicyclic, or tricyclic, and in addition in each case can be benzocondensed.

For example, there can be mentioned:

Thienyl, furanyl, pyrrolyl, oxazolyl, thiazolyl, imidazolyl, pyrazolyl, isoxazolyl, isothiazolyl, oxadiazolyl, triazolyl, thiadiazolyl, etc., and benzo derivatives thereof, such as, e.g., benzofuranyl, benzothienyl, benzoxazolyl, benzimidazolyl, indazolyl, indolyl, isoindolyl, etc.; or pyridyl, pyridazinyl, pyrimidinyl, pyrazinyl, triazinyl, etc., and benzo derivatives thereof, such as, e.g., quinolyl, isoquinolyl, etc.; or azocinyl, indolizinyl, purinyl, etc., and benzo derivatives thereof; or quinolinyl, isoquinolinyl, cinnolinyl, phthalazinyl, quinazolinyl, quinoxalinyl, naphthyridinyl, pteridinyl, carbazolyl, acridinyl, phenazinyl, phenothiazinyl, phenoxazinyl, xanthenyl, or oxepinyl, etc.

The heteroaryl radical can be benzocondensed in each case. For example, there can be mentioned as 5-ring heteroaromatic compounds: thiophene, furan, oxazole, thiazole, imidazole, pyrazole and benzo derivatives thereof, and as 6-ring heteroaromatic compounds: pyridine, pyrimidine, triazine, quinoline, isoquinoline and benzo derivatives.

Heteroatoms are defined as oxygen, nitrogen or sulfur atoms.

A 3- to 8-membered ring in the meaning of $R^2$, $R^3$, Y and Z, which is formed together with the nitrogen atom, is defined as $C_3$–$C_8$-cycloheteroalkyls and $C_3$–$C_8$-heteroaryls.

If an acid group is included, the physiologically compatible salts of organic and inorganic bases are suitable as salts, such as, for example, the readily soluble alkali salts and alkaline-earth salts as well as N-methyl-glucamine, dimethyl-glucamine, ethyl-glucamine, lysine, 1,6-hexadiamine, ethanolamine, glucosamine, sarcosine, serinol, tris-hydroxymethyl-amino-methane, aminopropanediol, Sovak base, and 1-amino-2,3,4-butanetriol.

If a basic group is included, the physiologically compatible salts of organic and inorganic acids are suitable, such as hydrochloric acid, sulfuric acid, phosphoric acid, citric acid, tartaric acid, fumaric acid, i.a.

The compounds of general formula I according to the invention also contain the possible tautomeric forms and comprise the E-isomers or Z-isomers, or, if a chiral center is present, also the racemates and enantiomers.

Those compounds of general formula I in which

X stands for CH,

W stands for hydrogen,

A, B, D,

E and Q as a ring together stand for pyridyl, $R^1$ stands for aryl or heteroaryl, which optionally can be substituted in one or more places in the same way or differently with halogen, hydroxy, $C_1$–$C_6$-alkyl, $C_3$–$C_6$-cycloalkyl, $C_4$–$C_6$-alkenyl, $C_2$–$C_6$-alkinyl, aralkyloxy, $C_1$–$C_6$-alkoxy, halo-$C_1$–$C_6$-alkyl, cyano-$C_1$–$C_6$-alkyl, or with the group =O, —SO$_2$R$^6$ or —OR$^5$, whereby $C_1$–$C_6$-alkyl optionally also can be substituted with the group —OR$^5$ or —NR$^9$R$^{10}$, Y and Z, in each case independently of one another, stand for a bond, $R^2$ and $R^3$, independently of one another, stand for hydrogen or for the group —$CONR^9R^{10}$, —$SO_2R^6$, —$COR^{11}$, —$COC_1$–$C_6$-alkyl, —$CO$—$C_1$–$C_6$-alkyl-$R^{11}$, —$NR^9R^{10}$ or for $C_1$–$C_6$-alkyl, $C_3$–$C_6$-cycloalkyl, $C_3$–$C_6$-cycloalkenyl, aryl or heteroaryl that is optionally substituted in one or more places in the same way or differently with halogen, cyano, $C_1$–$C_6$-alkyl, $C_1$–$C_6$-alkoxy, hydroxy-$C_1$–$C_6$-alkyl, halo-$C_1$–$C_6$-alkyl or with the group —$NR^7R^8$, —$OR^5$, —$C_1$–$C_6$-alkyl-$OR^5$, —$SR^4$, —$SOR^4$ or —$SO_2R^6$, or $R^2$, $R^3$, Y and Z together with the nitrogen atom form a 3- to 8-membered saturated or unsaturated ring, which optionally can contain additional heteroatoms in the ring and optionally can be substituted in one or more places in the same way or differently with halogen, cyano, $C_1$–$C_{12}$-alkyl, $C_1$–$C_{12}$-alkoxy, halo-$C_1$–$C_6$-alkyl, hydroxy-$C_1$–$C_6$-alkyl or with the group =O, —$OR^5$, —$SR^4$, —$SOR^4$ or —$SO_2R^6$, $R^4$ stands for $C_1$–$C_6$-alkyl, aryl or heteroaryl, $R^5$ stands for hydrogen, $C_1$–$C_6$-alkyl, halo-$C_1$–$C_6$-alkyl, $C_1$–$C_{12}$-alkoxy, $C_3$–$C_{10}$-cycloalkyl or halo-$C_3$–$C_6$-cycloalkyl, $R^6$ stands for hydrogen, $C_1$–$C_6$-alkyl, halo-$C_1$–$C_6$-alkyl, aryl or heteroaryl, or for the group —$NR^9R^{10}$, whereby the aryl or heteroaryl itself optionally can be substituted in one or more places in the same way or differently with $C_1$–$C_6$-alkyl, $C_1$–$C_6$-alkoxy, halogen or halo-$C_1$–$C_6$-alkoxy, $R^7$ and $R^8$, independently of one another, stand for hydrogen or $C_1$–$C_6$-alkyl, $R^9$ and $R^{10}$, independently of one another, stand for hydrogen, $C_1$–$C_6$-alkyl, $C_2$–$C_6$-alkenyl, aryl, $C_3$–$C_8$-cycloalkyl, or for the group —$CONR^7R^8$, or for $C_1$–$C_6$-alkyl that is optionally substituted in one or more places in the same way or differently with aryl, morpholino, hydroxy, halogen or $C_1$–$C_{12}$-alkoxy, or with the group —$NR^7R^8$, whereby the aryl itself optionally can be substituted in one or more places in the same way or differently with $C_1$–$C_6$-alkoxy or halo-$C_1$–$C_6$-alkyl, and $R^{11}$ stands for $C_1$–$C_6$-alkyl, $C_1$–$C_6$-alkoxy, hydroxy-$C_1$–$C_6$-alkyl, hydroxy-$C_1$–$C_6$-alkoxy, $C_3$–$C_6$-cycloalkyl, phenyl, pyridyl, biphenyl or naphthyl, whereby the phenyl itself can be substituted in one or more places in the same way or differently with $C_1$–$C_6$-alkyl, or halo-$C_1$–$C_6$-alkyl, as well as isomers, diastereomers, tautomers and salts thereof, have proven advantageous.

Those compounds of general formula I, in which

X stands for CH,

W stands for hydrogen,

A, B, D,

E, and Q as a ring together stand for pyridyl, $R^1$ stands for phenyl, quinolinyl, isoquinolinyl or indazolyl, which optionally can be substituted in one or more places in the same way or differently with halogen, hydroxy, $C_1$–$C_6$-alkyl, $C_2$–$C_6$-alkinyl, $C_1$–$C_6$-alkoxy, halo-$C_1$–$C_6$-alkyl, or cyano-$C_1$–$C_6$-alkyl, whereby $C_1$–$C_6$-alkyl optionally also can be substituted with the group —$OR^5$ or —$NR^9R^{10}$, Y and Z, in each case independently of one another, stand for a bond, or for the group =CO, $R^2$ and $R^3$, independently of one another, stand for hydrogen or for the group —$CONR^9R^{10}$, —$SO_2R^6$, —$COR^{11}$, —$COC_1$–$C_6$-alkyl, —$CO$—$C_1$–$C_6$-alkyl-$R^{11}$, —$NR^9R^{10}$ or for $C_1$–$C_6$-alkyl or phenyl that is optionally substituted in one or more places in the same way or differently with the group —$NR^7R^8$ or —$OR^5$, or $R^2$, $R^3$, Y and Z together with the nitrogen atom form a 3- to 8-membered saturated or unsaturated ring that optionally can contain additional heteroatoms in the ring and optionally can be substituted in one or more places in the same way or differently with halogen, cyano, $C_1$–$C_{12}$-alkyl, $C_1$–$C_{12}$-alkoxy, halo-$C_1$–$C_6$-alkyl, hydroxy-$C_1$–$C_6$-alkyl or with the group =O, —$OR^5$, —$SR^4$, —$SOR^4$ or —$SO_2R^6$, $R^5$ stands for hydrogen or $C_1$–$C_6$-alkyl, $R^6$ stands for hydrogen, $C_1$–$C_6$-alkyl, halo-$C_1$–$C_6$-alkyl, phenyl, benzyl, thiophenyl, or pyridyl, whereby the phenyl, benzyl, thiophenyl and pyridyl itself optionally can be substituted in one or more places in the same way or differently with $C_1$–$C_6$-alkyl, $C_1$–$C_6$-alkoxy, halogen or halo-$C_1$–$C_6$-alkoxy, $R^7$ and $R^8$, independently of one another, stand for hydrogen or $C_1$–$C_6$-alkyl, $R^9$ and $R^{10}$, independently of one another, stand for hydrogen, $C_1$–$C_6$-alkyl, $C_2$–$C_6$-alkenyl, phenyl, biphenyl, $C_3$–$C_8$-cycloalkyl, naphthyl or for the group —$CONR^7R^8$ or for $C_1$–$C_6$-alkyl that is optionally substituted in one or more places in the same way or differently with phenyl, morpholino, hydroxy, halogen, $C_1$–$C_{12}$-alkoxy, or with the group —$NR^7R^8$, whereby the phenyl itself optionally can be substituted in one or more places in the same way or differently with $C_1$–$C_6$-alkoxy or halo-$C_1$–$C_6$-alkyl, and $R^{11}$ stands for $C_1$–$C_6$-alkyl, $C_1$–$C_6$-alkoxy, hydroxy-$C_1$–$C_6$-alkyl, hydroxy-$C_1$–$C_6$-alkoxy, $C_3$–$C_6$-cycloalkyl, phenyl, pyridyl, biphenyl or naphthyl, whereby the phenyl itself can be substituted in one or more places in the same way or differently with $C_1$–$C_6$-alkyl, or halo-$C_1$–$C_6$-alkyl, as well as isomers, diastereomers, tautomers and salts thereof, are of special interest.

The compounds according to the invention as well as their physiologically compatible salts prevent a tyrosine phosphorylation or stop persistent angiogenesis and thus the growth and propagation of tumors, whereby they are distinguished in particular by a slighter inhibition of isoforms of Cytochrome P 450 (3A4). Medication using the compounds according to the invention can therefore be done at no risk even without regard to pharmaceutical agents that are administered at the same time and that are degraded via these isoforms.

The compounds of formula I as well as their physiologically compatible salts can be used as pharmaceutical agents based on their inhibitory activity relative to the phosphorylation of the VEGF receptor. Based on their profile of action, the compounds according to the invention are suitable for treating diseases that are caused or promoted by persistent angiogenesis.

Since the compounds of formula I are identified as inhibitors of the tyrosine kinases KDR and FLT, they are suitable in particular for treating those diseases that are caused or promoted by persistent angiogenesis that is triggered via the VEGF receptor or by an increase in vascular permeability.

The subject of this invention is also the use of the compounds according to the invention as inhibitors of the tyrosine kinases KDR and FLT.

Subjects of this invention are thus also pharmaceutical agents for treating tumors or use thereof.

The compounds according to the invention can be used either alone or in a formulation as pharmaceutical agents for treating tumor or metastasis growth, psoriasis, Kaposi's sarcoma, restenosis, such as, e.g., stent-induced restenosis, endometriosis, Crohn's disease, Hodgkin's disease, leukemia; arthritis, such as rheumatoid arthritis, hemangioma, angiofibroma; eye diseases, such as diabetic retinopathy, neovascular glaucoma; renal diseases, such as glomerulonephritis, diabetic nephropathy, malignant nephrosclerosis, thrombic microangiopathic syndrome, transplant rejections and glomerulopathy; fibrotic diseases, such as cirrhosis of the liver, mesangial cell proliferative diseases, arteriosclerosis, injuries to nerve tissue, and for inhibiting the reocclusion of vessels after balloon catheter treatment, in vascular prosthetics or after mechanical devices are used to keep vessels open, such as, e.g., stents, as immunosuppressive agents, for supporting scar-free healing, in senile keratosis and in contact dermatitis.

In treating injuries to nerve tissue, quick scar formation on the injury sites can be prevented with the compounds according to the invention, i.e., scar formation is prevented from occurring before the axons reconnect. A reconstruction of the nerve compounds was thus facilitated.

The formation of ascites in patients can also be suppressed with the compounds according to the invention. VEGF-induced edemas can also be suppressed.

Lymphangiogenesis plays an important role in lymphogenic metastasizing (Karpanen, T. et al., Cancere Res. 2001 Mar 1, 61(5): 1786–90, Veikkola, T., et al., EMBO J. 2001, Mar 15; 20 (6): 1223–31).

The compounds according to the invention now also show excellent action as VEGFR kinase 3 inhibitors and are therefore also suitable as effective inhibitors of lymphangiogenesis.

By a treatment with the compounds according to the invention, not only a reduction of the size of metastases but also a reduction of the number of metastases is achieved.

Such pharmaceutical agents, their formulations and uses are also subjects of this invention.

The invention thus also relates to the use of the compounds of general formula I for the production of a pharmaceutical agent for use as or for treatment of tumor or metastasis growth, psoriasis, Kaposi's sarcoma, restenosis, such as, e.g., stent-induced restenosis, endometriosis, Crohn's disease, Hodgkin's disease, leukemia; arthritis, such as rheumatoid arthritis, hemangioma, angiofibroma; eye diseases, such as diabetic retinopathy, neovascular glaucoma; renal diseases, such as glomerulonephritis, diabetic nephropathy, malignant nephrosclerosis, thrombic microangiopathic syndrome, transplant rejections and glomerulopathy; fibrotic diseases, such as cirrhosis of the liver, mesangial cell proliferative diseases, arteriosclerosis, injuries to nerve tissue, and for inhibiting the reocclusion of vessels after balloon catheter treatment, in vascular prosthetics or after mechanical devices are used to keep vessels open, such as, e.g., stents, as immunosuppressive agents, as a support in scar-free healing, in senile keratosis and in contact dermatitis.

The formation of ascites in patients can also be suppressed with the compounds according to the invention. VEGF-induced edemas can also be suppressed.

To use the compounds of formula I as pharmaceutical agents, the latter are brought into the form of a pharmaceutical preparation, which in addition to the active ingredient for enteral or parenteral administration contains suitable pharmaceutical, organic or inorganic inert carrier materials, such as, for example, water, gelatin, gum arabic, lactose, starch, magnesium stearate, talc, vegetable oils, polyalkylene glycols, etc. The pharmaceutical preparations can be present in solid form, for example as tablets, coated tablets, suppositories, or capsules, or in liquid form, for example as solutions, suspensions or emulsions. They optionally contain, moreover, adjuvants such as preservatives, stabilizers, wetting agents or emulsifiers, salts for changing osmotic pressure or buffers.

For parenteral administration, especially injection solutions or suspensions, especially aqueous solutions of the active compounds in polyhydroxyethoxylated castor oil, are suitable.

As carrier systems, surface-active adjuvants such as salts of bile acids or animal or plant phospholipids, but also mixtures thereof as well as liposomes or components thereof can also be used.

For oral administration, especially tablets, coated tablets or capsules with talc and/or hydrocarbon vehicles or binders, such as for example, lactose, corn starch or potato starch, are suitable. The administration can also be carried out in liquid form, such as, for example, as juice, to which optionally a sweetener or, if necessary, one or more flavoring substances, is added.

The dosage of the active ingredients can vary depending on the method of administration, age and weight of the patient, type and severity of the disease to be treated and similar factors. The daily dose is 0.5–1000 mg, preferably 50–200 mg, whereby the dose can be given as a single dose to be administered once or divided into 2 or more daily doses.

The above-described formulations and forms for dispensing are also subjects of this invention.

The production of the compounds according to the invention is carried out according to methods that are known in the art. For example, compounds of general formula I are obtained in that a compound of general formula II

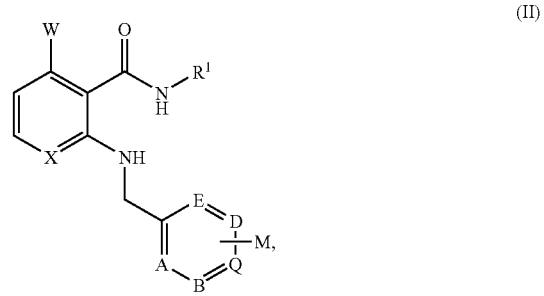

in which A, B, D, E, Q, W, X and $R^1$ have the meanings that are indicated in general formula I, and M stands for halogen, first is converted into an amine and then is acylated, or M is substituted by an NHCOR' group.

Compounds of general formula I are also obtained in that a compound of general formula IIa,

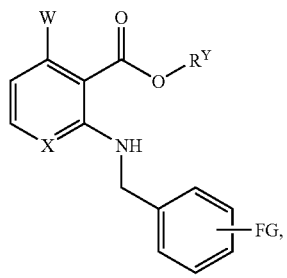

in which $R^y$ stands for $C_1$–$C_6$-alkyl or hydrogen, and FG means a leaving group, such as, e.g., halogen, O-triflate, O-mesylate, O-tosylate or sulfone, first is converted into an amide, and then the leaving group is substituted by an N(Y—$R^1$)—$R^3$ group, or a compound III

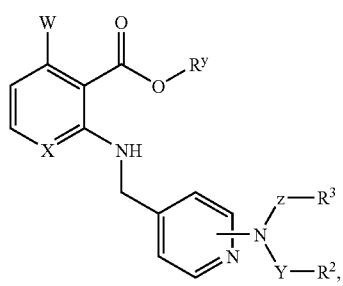

in which $R^2$, $R^3$, Y and Z have the meanings that are indicated in general formula I and $R^y$ stands for $C_1$–$C_6$-alkyl or hydrogen, first is saponified and then is converted into the amide.

The amide formation is carried out according to methods that are known in the literature.

For amide formation, it is possible to start from a corresponding ester. The ester is reacted according to J. Org. Chem. 1995, 8414 with aluminum trimethyl and the corresponding amine in solvents such as toluene at temperatures of 0° C. to the boiling point of the solvent. If the molecule contains two ester groups, both are converted into the same amide. Instead of aluminum trimethyl, sodium hexamethyldisilazide can also be used.

For amide formation, however, all processes that are known from peptide chemistry are also available. For example, the corresponding acid can be reacted with the amine in aprotic polar solvents, such as, for example, dimethylformamide, via an activated acid derivative, that can be obtained, for example, with hydroxybenzotriazole and a carbodiimide, such as, for example, diisopropylcarbodiimide, at temperatures of between 0° C. and the boiling point of the solvent, preferably at 80° C. The reaction between carboxylic acid and amine, however, can also be produced by activation reagents, such as HATU (N-dimethylamino-1H-1,2,3-triazolo-[4,5-b]pyridin-1-ylmethylene]-N-methylmethanaminium hexafluorophosphate-N-oxide), whereby polar aprotic solvents, such as, for example, dimethylformamide, are suitable for the reaction. The addition of a base such as N-methylmorpholine is necessary. The reaction proceeds at temperatures of 0–100° C., whereby the procedure is preferably performed at room temperature, but in many cases heating is indispensable. For the amide formation, the process can also be used with the acid halide, the mixed acid anhydride, imidazolide or azide. A previous protection of an additional amino group, for example as an amide, is not necessary in all cases, but can advantageously influence the reaction.

In the case of bisacid chlorides, cyclic compounds can be produced. Also, in the case of halogen acid halides, cyclic compounds can be produced. The ring closure is then completed optionally by adding a strong base, such as, for example, sodium alcoholates. The same thing holds true for the sulfonic acid halides, whereby double sulfonations can also occur.

Ureas are produced from amino compounds by reaction with isocyanates. Inert solvents such as methylene chloride or else dimethylformamide at temperatures from room temperature up to 100° C., preferably at 60° C. Pressure is advantageous for the reaction.

The reaction of halopyridines with amides is carried out under catalysis, for example by palladium or copper catalysis. In the case of copper catalysis (literature, see Synlett. 2002, 427), solvents such as dioxane or dimethylformamide are used at temperatures up to the boiling point of the solvent, preferably 120° C. As a base, potassium phosphate or else cesium carbonate is used. Ethylenediamine is advantageous for complexing the copper(I) iodide that is used as a catalyst. An application of pressure is not harmful. In the case of palladium catalysis, both palladium(II) salts, such as palladium(II) acetate, and palladium(O) complexes, such as palladium(O)$_2$dibenzylidene acetone$_3$ (literature, see JACS 2002, 6043, THL 1999, 2035, Org. Lett 2001, 2539, THL 2001, 4381 or THL 2001, 3681) can . . . . As a solvent, toluene, dioxane or dimethylformamide are used at temperatures from room temperature up to the boiling point of the solvent, preferably around 100° C. As a co-ligand, BINAP, DPPF or Xanthphos are used. A base is also necessary. To this end, cesium carbonate, potassium phosphate or else sodium-t-butylate is used. These components can be combined in various ways.

The production of the pyridinamines from the corresponding 2-halopyridines is carried out in solvents such as pyridine or in protic polar solvents such as ethylene glycol at temperatures up to 200° C. Catalysis by copper(I) salts can be necessary for the reaction. The application of pressure is absolutely necessary in the case of the reaction of low-boiling amines, but can also be used advantageously in the conventional amines.

The ether cleavage is accomplished according to known methods, for example by reaction with boron tribromide in inert solvents, such as methylene chloride, at temperatures of –78° C. up to room temperature, preferably at –78° C.

The compounds of general formulas II, IIa and III,

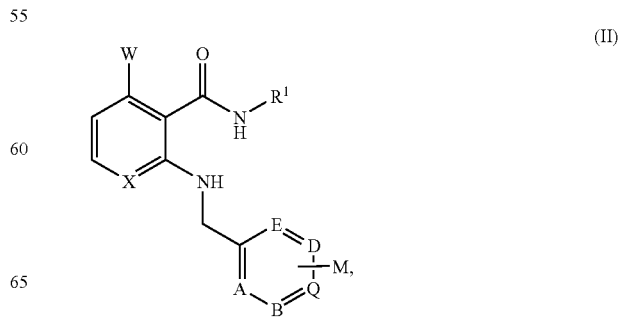

-continued

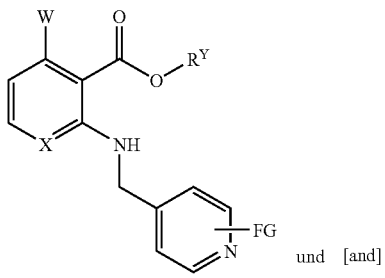

und [and]

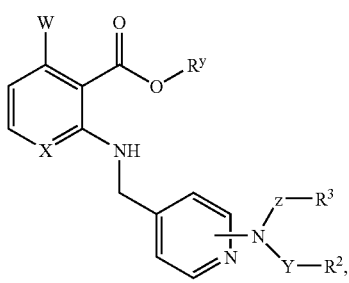

in which A, B, D, E, Q, W, X, Y, Z, R², and R³ have the meanings that are indicated in general formula I and M stands for halogen, FG stands for a leaving group, such as, e.g., halogen, O-triflate, O-mesylate, O-tosylate or sulfone, and $R^Y$ stands for $C_1$–$C_6$-alkyl or hydrogen, represent valuable intermediate products for the production of the compounds of general formula I according to the invention and are thus also subjects of this invention.

PRODUCTION OF THE COMPOUNDS ACCORDING TO THE INVENTION

The following examples explain the production of the compounds according to the invention without the scope of the claimed compounds being limited to these examples.

EXAMPLE 1.0

Production of 2-{[2-(2-Dimethylamino-ethylamino)-pyridin-4-ylmethyl]-amino}-N-(3-trifluoromethyl-phenyl)-benzamide

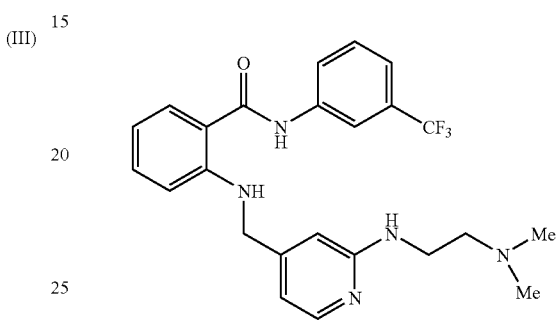

90 mg (0.2 mmol) of 2-[(2-bromo-pyridin-4-ylmethyl)-amino]-N-(3-trifluoromethyl-phenyl)-benzamide is dissolved in 3 ml of pyridine and mixed with 1 ml of N,N-dimethyl-aminoethylamine and heated in a pressure vessel for 5 hours to a bath temperature of 200° C. After cooling, it is concentrated by evaporation, and 90 mg of 2-{[2-(2-dimethylamino-ethylamino)-pyridin-4-ylmethyl]-amino}-N-(3-trifluoromethyl-phenyl)-benzamide is obtained.

Melting point: 100° C.

Similarly produced are also the following compounds:

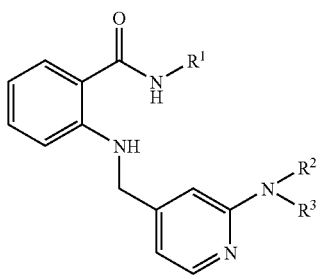

Typ A

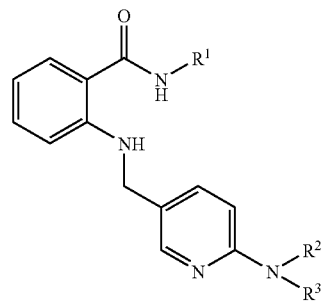

Typ B

[Key: Typ = Type]

| Example No. | Type | R² | R³ | R¹ | MW | Melting Point [° C.] or MS Molar Peak (m/e) |
|---|---|---|---|---|---|---|
| 1.1 | A | —(CH₂)₂—OH | H | 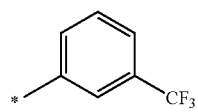 | | 430.5 |

-continued
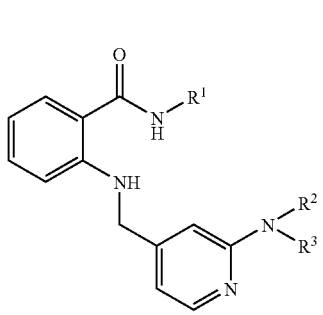
Typ A
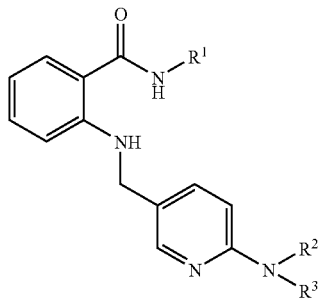
Typ B
[Key: Typ = Type]
| Example No. | Type | R² | R³ | R¹ | MW | Melting Point [° C.] or MS Molar Peak (m/e) |
|---|---|---|---|---|---|---|
| 1.2 | A | —(CH$_2$)$_2$—OH | H | isoquinolin-3-yl | 413.5 | 130–132 |
| 1.3 | A | —(CH$_2$)$_3$OH | H | 3-CF$_3$-phenyl | 444.5 | 148 |
| 1.4 | A | —(CH$_2$)$_4$OH | H | 3-CF$_3$-phenyl | 458.5 | 124 |
| 1.5 | A | —(CH$_2$)$_5$OH | H | 3-CF$_3$-phenyl | 472.5 | 70 |
| 1.6 | A | —(CH$_2$)$_2$OMe | H | 3-CF$_3$-phenyl | 444.5 |  |
| 1.7 | A | (R)-*-CH$_2$-CH(OH)-CH$_3$ | H | 3-CF$_3$-phenyl | 444.5 | 80 |
| 1.8 | A | (S)-*-CH$_2$-CH(OH)-CH$_3$ | H | 3-CF$_3$-phenyl | 444.5 | 65 |
| 1.9 | A | (S)-*-CH(CH$_3$)-CH$_2$OH | H | 3-CF$_3$-phenyl | 444.5 | 81 |
| 1.10 | A | (CH$_2$)$_3$NMe$_2$ | H | 3-CF$_3$-phenyl | 471.5 | 68 |

-continued
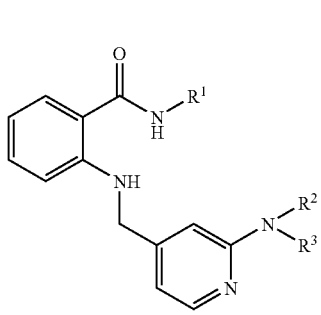
Typ A
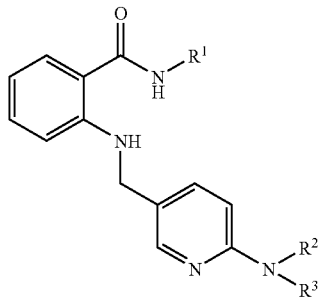
Typ B
[Key: Typ = Type]
| Example No. | Type | R² | R³ | R¹ | MW | Melting Point [° C.] or MS Molar Peak (m/e) |
|---|---|---|---|---|---|---|
| 1.11 | B | —(CH₂)₂—OH | H | isoquinolin-3-yl | 413.5 | Resin |
| 1.12 | A | Phenyl | H | 3-(trifluoromethyl)phenyl | 462.5 | |
| 1.13 | A | —(CH₂)₅— | | isoquinolin-3-yl | 437.54 | |
| 1.14 | A | —(CH₂)₂—O—(CH₂)₂— | | isoquinolin-3-yl | 439.52 | 174 |
| 1.15 | A | —(CH₂)₂—NMe—(CH₂)₂— | | isoquinolin-3-yl | 452.56 | 85 |
| 1.16 | A | —(CH₂)₂—S—(CH₂)₂— | | isoquinolin-3-yl | 455.58 | 158 |
| 1.17 | A | —(CH₂)₂—SO₂—(CH₂)₂— | | isoquinolin-3-yl | 487.58 | |
| 1.18 | A | —(CH₂)₄— | | isoquinolin-3-yl | 423.52 | 148 |

EXAMPLE 2.0

Production of 2-[(2-Amino-pyridin-4-ylmethyl)-amino]-N-(3-trifluoromethyl-phenyl)-benzamide

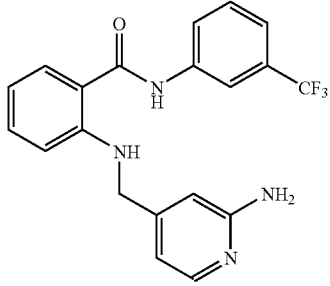

8.747 g (19.4 mmol) of 2-[(2-bromo-pyridin-4-ylmethyl)-amino]-N-(3-trifluoromethyl-phenyl)-benzamide is heated with 175 mg of copper(I) oxide in 150 ml of ethanediol for 23 hours under 10 bar of ammonia pressure to 80° C. in an autoclave. After the solvent is distilled off in a vacuum, the residue is purified on silica gel with a gradient of ethyl acetate:ethanol=100:0 to 0:100 as an eluant. 4.15 g (51% of theory) of 2-[(2-amino-pyridin-4-ylmethyl)-amino]-N-(3-trifluoromethyl-phenyl)-benzamide with a melting point of 64° C. is obtained.

Similarly produced are:

EXAMPLE 2.1

2-[(2-Amino-pyridin-4-ylmethyl)-amino]-N-isoquinolin-3-yl-benzamide

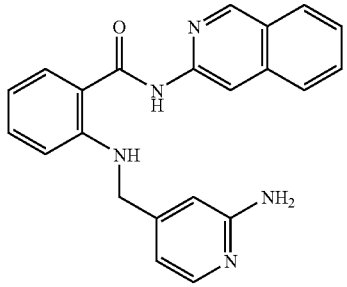

Melting point: 202° C.

EXAMPLE 2.2

2-[(2-Amino-pyridin-4-ylmethyl)-amino]-N-(1H-indazol-5-yl)-benzamide

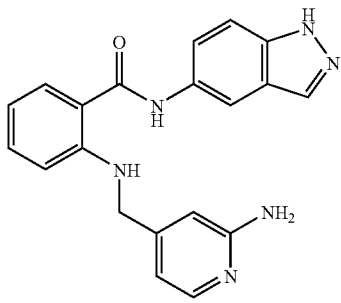

MS: m/e 358
Melting point: 200° C.

EXAMPLE 2.3

2-[(2-Amino-pyridin-4-ylmethyl)-amino]-N-(2-methyl-2H-indazol-6-yl)-benzamide

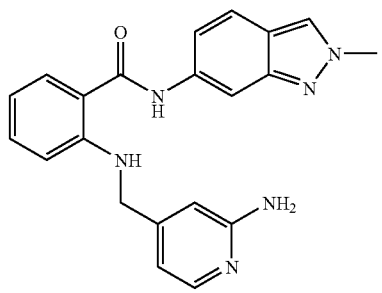

MW: 372.43

EXAMPLE 3.0

Production of 2-{[2-(3-Benzyl-ureido)-pyridin-4-ylmethyl]-amino}-N-(3-trifluoromethyl-phenyl)-benzamide

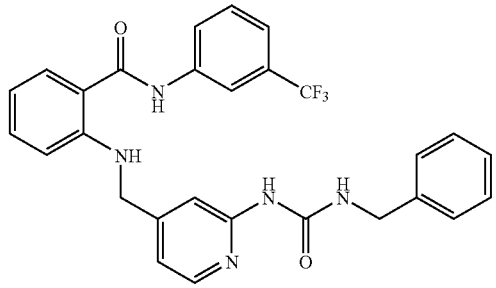

100 mg (0.26 mmol) of 2-[(2-amino-pyridin-4-ylmethyl)-amino]-N-(3-trifluoromethyl-phenyl)-benzamide is mixed in 2.5 ml of methylene chloride with 37.9 mg (0.29 mmol) of benzyl isocyanate, and it is stirred overnight at room temperature. After concentration by evaporation, the residue is chromatographed. 66 mg (49% of theory) of 2-{[2-(3-benzyl-ureido)-pyridin-4-ylmethyl]-amino}-N-(3-trifluoromethyl-phenyl)-benzamide with a melting point of 153° C. is obtained.

Similarly produced are also the following compounds:

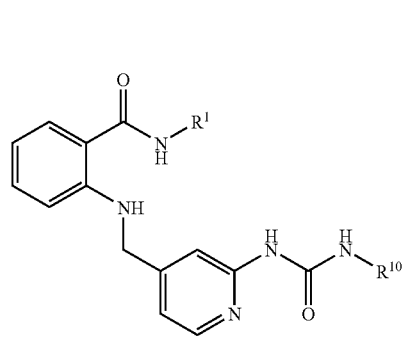
Typ A
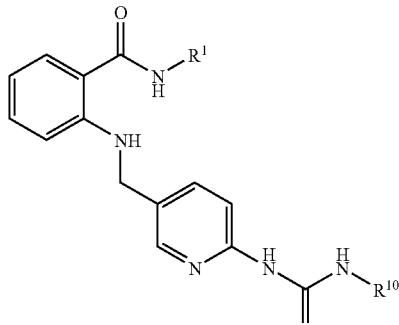
Typ B
[Key: Typ = Type]
| Example No. | Type | R¹ | R¹⁰ | MW | Melting Point [° C.] or MS Molar Peak (m/e) |
|---|---|---|---|---|---|
| 3.1 | A | 3-CF₃-phenyl | Phenyl | 505.5 | 185 |
| 3.2 | A | 3-CF₃-phenyl | Ph(CH₂)₂— | 533.5 | 76 |
| 3.3 | A | 3-CF₃-phenyl | n-Butyl | 485.5 | 84 |
| 3.4 | A | 3-CF₃-phenyl | 3,4,5-(OMe)₃-phenyl | 595.5 | 206 |
| 3.5 | A | 3-CF₃-phenyl | 3-CF₃-phenyl | 573.5 | 186 |
| 3.6 | A | 3-CF₃-phenyl | 4-CF₃-phenyl | 573.5 | 211 |
| 3.7 | A | 3-CF₃-phenyl | Ethyl | 457.5 | 154 |

-continued
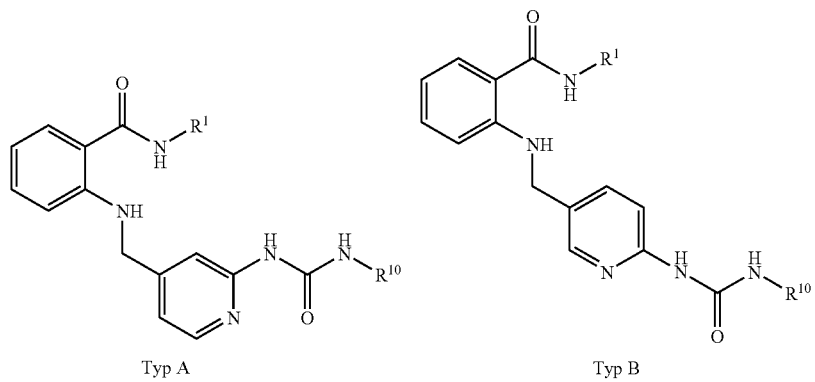
Typ A                    Typ B
[Key: Typ = Type]
| Example No. | Type | R¹ | R¹⁰ | MW | Melting Point [° C.] or MS Molar Peak (m/e) |
|---|---|---|---|---|---|
| 3.8 | A | *-C₆H₄-CF₃ (3-CF₃-phenyl) | 4-biphenyl | 581.6 | 195 |
| 3.9 | A | *-C₆H₄-CF₃ (3-CF₃-phenyl) | 1-naphthyl | 555.5 | 180 |
| 3.10 | A | *-C₆H₄-CF₃ (3-CF₃-phenyl) | —CH₃ | 443.4 | 159 |
| 3.11 | A | *-C₆H₄-CF₃ (3-CF₃-phenyl) | —CH₂CH₂Cl | 491.9 | 157 |
| 3.12 | A | *-C₆H₄-CF₃ (3-CF₃-phenyl) | n-Propyl | 471.5 | 80 |
| 3.13 | A | *-C₆H₄-CF₃ (3-CF₃-phenyl) | i-Propyl | 471.5 | 96 |
| 3.14 | A | *-C₆H₄-CF₃ (3-CF₃-phenyl) | cyclopentyl | 497.5 | 103 |

-continued
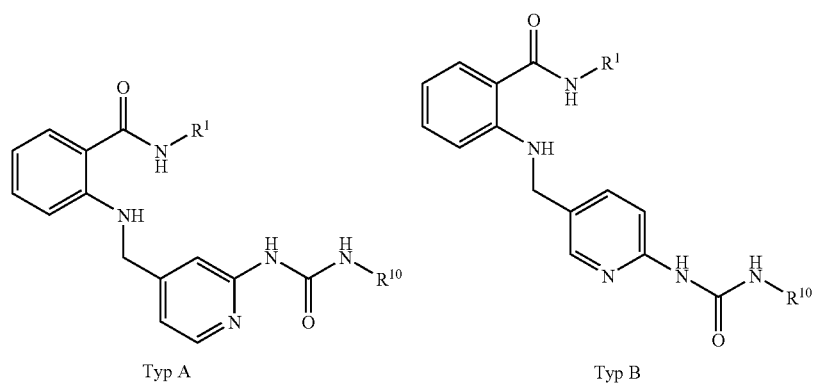
Typ A  Typ B
[Key: Typ = Type]
| Example No. | Type | R¹ | R¹⁰ | MW | Melting Point [° C.] or MS Molar Peak (m/e) |
|---|---|---|---|---|---|
| 3.15 | A | *-C₆H₄-3-CF₃ | —CONH₂ | 472.4 | 190 |
| 3.16 | A | 3-isoquinolinyl | 3,4,5-trimethoxyphenyl | 578.6 | 213 |
| 3.17 | A | 3-isoquinolinyl | *-C₆H₄-3-CF₃ | 556.5 | 203 |
| 3.18 | A | 3-isoquinolinyl | *-C₆H₄-4-CF₃ | 556.5 | 165 |
| 3.19 | A | 3-isoquinolinyl | phenyl | 488.5 | 198 |
| 3.20 | A | 3-isoquinolinyl | 1-naphthyl | 538.6 | 213 |
| 3.21 | A | 3-isoquinolinyl | benzyl | 502.6 | 185 |
| 3.22 | A | 3-isoquinolinyl | phenethyl | 516.6 | 171 |

-continued
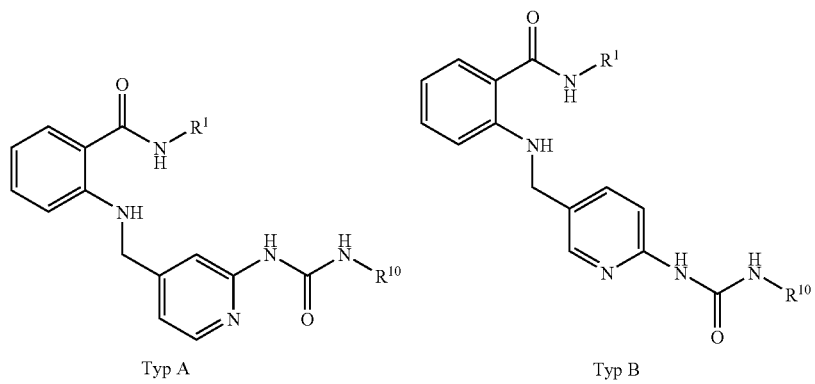
Typ A  Typ B
[Key: Typ = Type]
| Example No. | Type | R¹ | R¹⁰ | MW | Melting Point [° C.] or MS Molar Peak (m/e) |
|---|---|---|---|---|---|
| 3.23 | A | isoquinolinyl | —CH₂CH₂Cl | 474.9 | 195 |
| 3.24 | A | isoquinolinyl | —CH₃ | 426.5 | 225 |
| 3.25 | A | isoquinolinyl | n-Propyl | 454.5 | |
| 3.26 | A | isoquinolinyl | i-Propyl | 454.5 | |
| 3.27 | A | isoquinolinyl | Ethyl | 440.5 | |
| 3.28 | A | isoquinolinyl | cyclopentyl | 480.6 | 205 |
| 3.29 | A | isoquinolinyl | —CONH₂ | 455.5 | 129 |

Examples 3.15 and 3.29 are produced analogously to Example 3.0 with use of trimethylsilyl isocyanate.

EXAMPLE 3.30

Production of 2-{[2-(3,3-Dimethyl-ureido)-pyridin-4-ylmethyl]-amino}-N-(3-isoquinolinyl)-benzamide

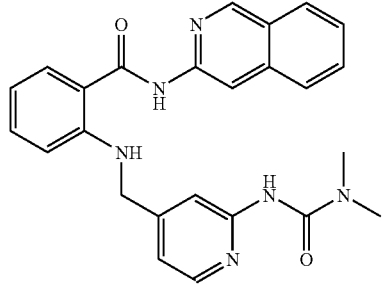

100 mg (0.23 mmol) of 2-[(2-bromopyridin-4-ylmethyl)-amino]-N-(3-isoquinolinyl)-benzamide is heated in 2 ml of dioxane with 89 mg (0.28 mmol) of cesium carbonate, 61 mg (0.69 mmol) of N,N-dimethylurea, 4.7 mg (0.0046 mmol) of dipalladium-tribenzylidene acetone and 7.9 mg (0.014 mmol) of Xanthphos under a cover gas and in a moisture-free environment for 9 hours to a bath temperature of 100° C. It is then mixed with 20 ml of methylene chloride, suctioned off and concentrated by evaporation. The residue is chromatographed on silica gel with ethyl acetate as an eluant. 24 mg (24% of theory) of 2-{[2-(3,3-dimethyl-ureido)-pyridin-4-ylmethyl]-amino}-N-(3-isoquinolinyl)-benzamide is obtained.

(MS (CI): 441 ($M^+$+H))

Similarly produced are also the following compounds:

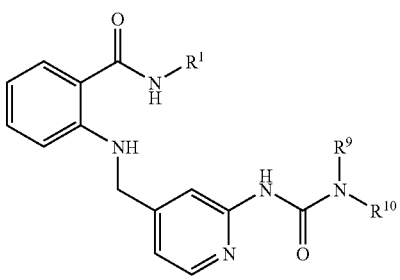

Typ A

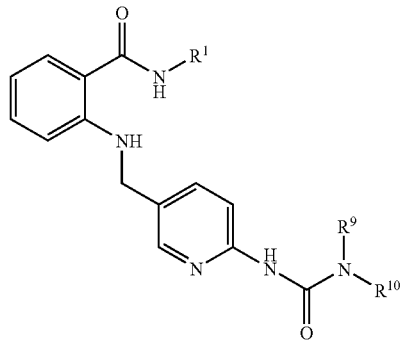

Typ B

[Key: Typ = Type]

| Example No. | Type | $R^1$ | $R^9$ | $R^{10}$ | MW | Melting Point [° C.] or MS Molar Peak (m/e) |
|---|---|---|---|---|---|---|
| 3.31 | A | isoquinolinyl | H | H | 412.5 | 222 |
| 3.32 | A | 3-CF₃-phenyl | H | H | 429.4 | |
| 3.33 | A | 1H-indazol-5-yl | Me | H | 415.46 | |
| 3.34 | A | 1H-indazol-6-yl | Me | H | 415.46 | 110–113 |

-continued
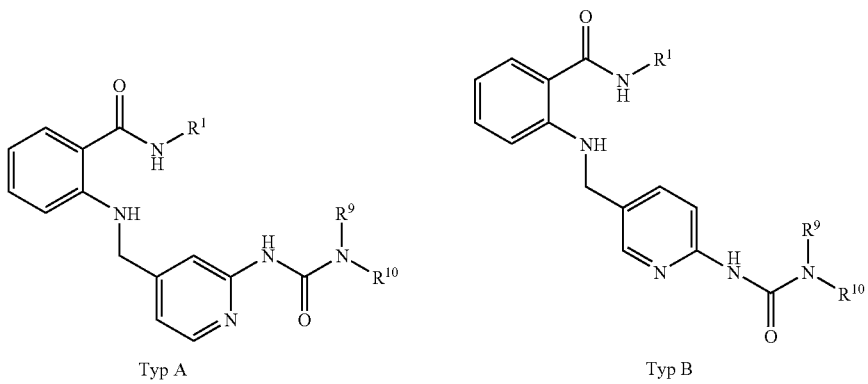
Typ A  Typ B
[Key: Typ = Type]
| Example No. | Type | R¹ | R⁹ | R¹⁰ | MW | Melting Point [° C.] or MS Molar Peak (m/e) |
|---|---|---|---|---|---|---|
| 3.35 | A | 6-(1-methylindazolyl) | Me | H | 429.48 | 230–232 |
| 3.36 | A | 6-(2-methylindazolyl) | Me | H | 429.48 | 130–133 |
| 3.37 | A | 5-(1-isopropylindazolyl) | Me | H | 457.54 | |
| 3.38 | A | 5-(2-methylindazolyl) | allyl | H | 455.52 | |
| 3.39 | A | 6-(1-methylindazolyl) | allyl | H | 455.52 | |
| 3.40 | A | 6-(1-methylindazolyl) | Me | Me | 443.51 | |
| 3.41 | A | 5-(2-methylindazolyl) | Me | Me | 443.51 | |

-continued
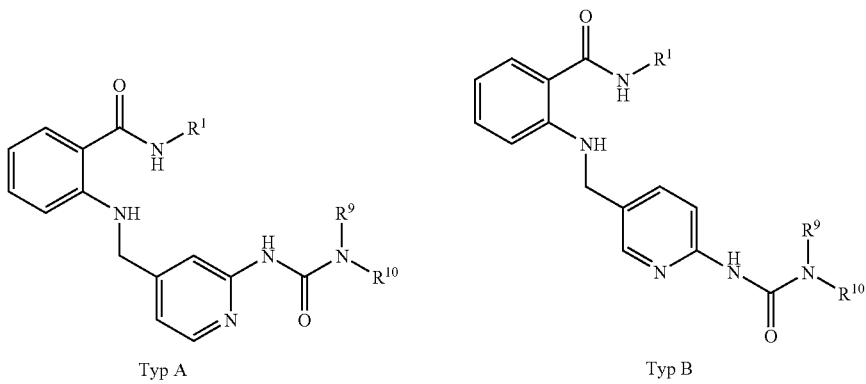
Typ A  Typ B
[Key: Typ = Type]
| Example No. | Type | R¹ | R⁹ | R¹⁰ | MW | Melting Point [° C.] or MS Molar Peak (m/e) |
|---|---|---|---|---|---|---|
| 3.42 | A | 6-indazolyl, N1-Et | Me | H | 443.51 | |
| 3.43 | A | 6-indazolyl, N1-i-Prop | Me | H | 457.54 | |
| 3.44 | A | 6-indazolyl, N2-Et | Me | H | 443.51 | |
| 3.45 | A | 6-indazolyl, N2-i-Prop | Me | H | 457.54 | |
| 3.46 | A | 5-indazolyl, N2-i-Prop | Me | H | 457.54 | |
| 3.47 | A | 5-indazolyl, N1-CH2CH2OMe | Me | H | 473.53 | 199.5 |
| 3.48 | A | 5-indazolyl, N1-Et | Me | H | 443.51 | 208.8 |
| 3.49 | A | 5-indazolyl, N1-propargyl | Me | H | 453.50 | 242 |

-continued
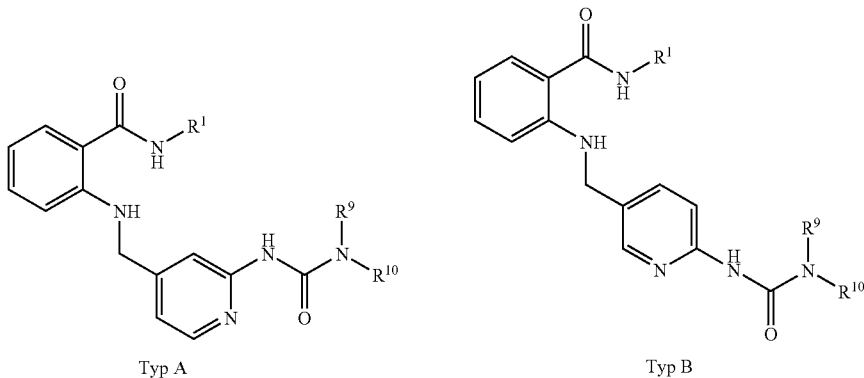
Typ A          Typ B
[Key: Typ = Type]
| Example No. | Type | R¹ | R⁹ | R¹⁰ | MW | Melting Point [° C.] or MS Molar Peak (m/e) |
|---|---|---|---|---|---|---|
| 3.50 | A | 5-(2-Me-indazolyl) | Me | H | 429.48 | m/e 429 |
| 3.51 | A | 5-(1-Me-indazolyl) | Me | H | 429.48 | 205.1 |
| 3.52 | A | 6-(1-Me-indazolyl) | cycl.Prop | H | 455.52 | 192 |
| 3.53 | A | 6-(2-Me-indazolyl) | cycl.Prop | H | 455.52 | 216 |
| 3.54 | A | 6-(1-(2-OMe-ethyl)-indazolyl) | Me | H | 473.53 | 247 |
| 3.55 | A | 6-(2-Me-indazolyl) | CH₂-morpholinyl | H | 499.57 | |
| 3.56 | A | 6-(2-(2-OMe-ethyl)-indazolyl) | Me | H | 473.53 | |
| 3.57 | A | 5-(2-(2-OMe-ethyl)-indazolyl) | Me | H | 473.53 | |

-continued
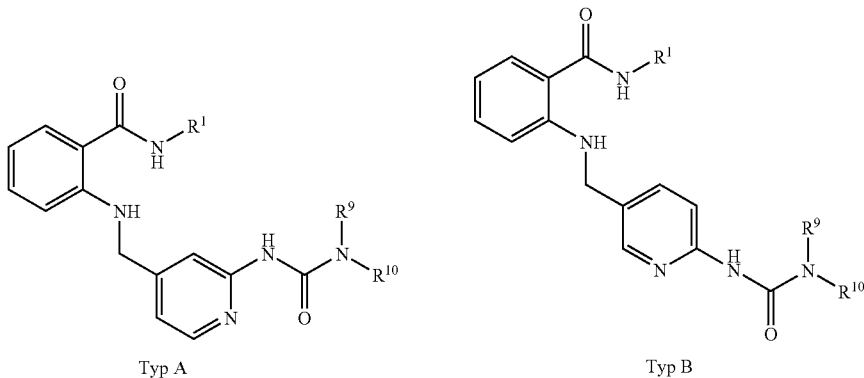
Typ A            Typ B
[Key: Typ = Type]
| Example No. | Type | R¹ | R⁹ | R¹⁰ | MW | Melting Point [° C.] or MS Molar Peak (m/e) |
|---|---|---|---|---|---|---|
| 3.58 | B | 2-Me-indazol-6-yl | Me | H | 429.48 | |
| 3.59 | B | 1-Me-indazol-6-yl | Me | H | 429.48 | |
| 3.60 | A | 2-(CH$_2$CN)-indazol-5-yl | Me | H | 454.48 | |
| 3.61 | A | 1-(CH$_2$CN)-indazol-5-yl | Me | H | 454.48 | |
| 3.62 | A | 2-(CH$_2$CH$_2$NMe$_2$)-indazol-5-yl | Me | H | 486.53 | |
| 3.63 | A | 2-Me-indazol-6-yl | —(CH$_2$)$_2$—O—CH$_3$ | H | 473.53 | |
| 3.64 | A | 2-Me-indazol-6-yl | —(CH$_2$)$_2$N(CH$_3$)$_2$ | H | 486.58 | |
| 3.65 | A | 2-Me-indazol-6-yl | 2-(morpholin-4-yl)ethyl | H | 528.61 | |

-continued

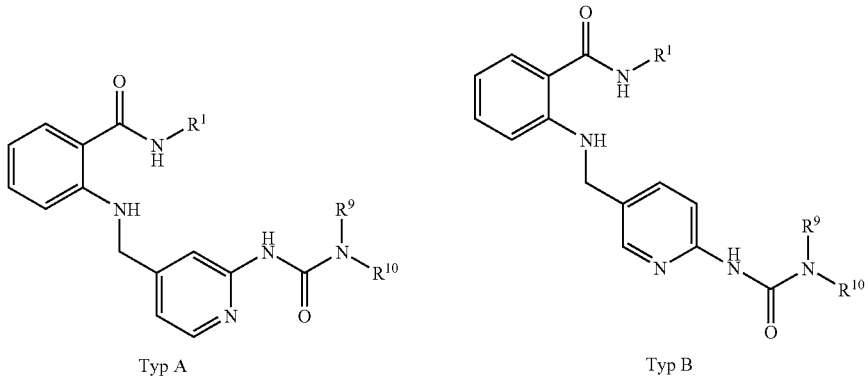

Typ A  Typ B

[Key: Typ = Type]

| Example No. | Type | R¹ | R⁹ | R¹⁰ | MW | Melting Point [° C.] or MS Molar Peak (m/e) |
|---|---|---|---|---|---|---|
| 3.66 | A | 6-indazolyl-N(Me) | —(CH$_2$)$_2$—O—CH$_3$ | H | 473.53 | |
| 3.67 | A | 6-indazolyl-N(Me) | —(CH$_2$)$_2$N(CH$_3$)$_2$ | H | 486.58 | |
| 3.68 | A | 6-indazolyl-N(Me) | propyl-morpholine | H | 528.61 | |
| 3.69 | A | 6-indazolyl-N(CH$_2$CN) | Me | H | 454.49 | |

EXAMPLE 4.0

Production of 2-[(2-Methanesulfonylamino-pyridin-4-ylmethyl)-amino]-N-(3-trifluoromethyl-phenyl)-benzamide

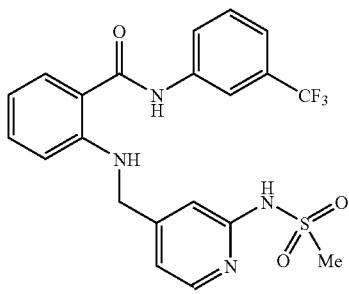

90 mg (0.2 mmol) of 2-[(2-bromo-pyridin-4-ylmethyl)-amino]-N-(3-trifluoromethyl-phenyl)-benzamide and 23 mg (0.24 mmol) of methanesulfonic acid amide are introduced into 5 ml of dioxane and mixed in succession with 4 mg (0.02 mmol) of copper(I) iodide, 85 mg (0.4 mmol) of potassium phosphate and 2 mg (0.02 mmol) of ethylenediamine. After 1 hour of stirring at a bath temperature of 120° C., it is diluted with 20 ml of water and concentrated by evaporation. It is then made alkaline with ammonia and shaken out three times with 25 ml each of ethyl acetate. The collected organic phase is washed with water, dried, filtered and concentrated by evaporation. The residue is made crystalline with ethyl acetate and a little hexane, stirred and suctioned off. 24 mg (26% of theory) of 2-[(2-methanesulfonyl-amino-pyridin-4-ylmethyl)-amino]-N-(3-trifluoromethyl-phenyl)-benzamide with a melting point of 214.5° C. is obtained.

Similarly produced are:

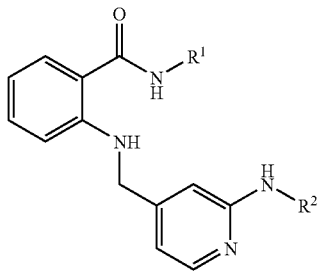
| Example No. | R¹ | R² | MW | Melting Point [° C.] or MS Molar Peak (m/e) |
|---|---|---|---|---|
| 4.1 | *-C₆H₄-CF₃ (3-) | *-SO₂-C₆H₅ | 526.54 | 259.2 |
| 4.2 | *-C₆H₄-CF₃ (3-) | *-SO₂-(2-pyridyl)-5-Me | 541.55 | >300 |
| 4.3 | *-C₆H₄-CF₃ (3-) | *-SO₂-C₆H₄-OCF₃ (4-) | 610.53 | 248.6 |
| 4.4 | *-C₆H₄-CF₃ (3-) | —SO₂CF₃ | 518.44 | 238.9 |
| 4.5 | *-(3-isoquinolinyl) | —SO₂CH₃ | 447.52 | m/e: 447 |
| 4.6 | *-C₆H₄-CF₃ (3-) | *-SO₂-C₆H₃-3,4-F₂ | 562.52 | 252.5 |
| 4.7 | *-C₆H₄-CF₃ (3-) | *-SO₂-C₆H₄-OnBu (4-) | 598.64 | 231 |
| 4.8 | *-C₆H₄-CF₃ (3-) | *-SO₂-(2-thienyl)-5-Cl | 567.01 | 255.2 |
| 4.9 | *-(3-isoquinolinyl) | *-SO₂-(2-thienyl)-5-Cl | 550.06 | 234.7 |

-continued

| Example No. | R¹ | R² | MW | Melting Point [° C.] or MS Molar Peak (m/e) |
|---|---|---|---|---|
| 4.10 | 3-(trifluoromethyl)phenyl | 4-methylphenylsulfonyl | 540.56 | 245.7 |
| 4.11 | 3-(trifluoromethyl)phenyl | benzylsulfonyl | 540.56 | 194.8 |
| 4.12 | 1H-indazol-5-yl | phenylsulfonyl | 498.57 | 256 |
| 4.13 | 1H-indazol-5-yl | 4-methylphenylsulfonyl | 512.59 | 219 |

EXAMPLE 5.0

Production of 2-[(2-Bismethanesulfonylamino-pyridin-4-ylmethyl)-amino]-N-(3-trifluoromethyl-phenyl)-benzamide

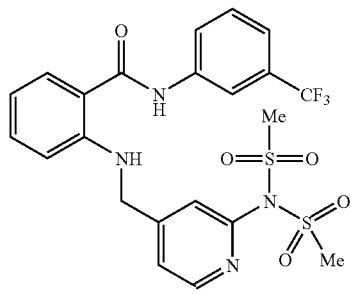

193 mg (0.5 mmol) of 2-[(2-amino-pyridin-4-ylmethyl)-amino]-N-(3-trifluoromethyl-phenyl)-benzamide is mixed in 3 ml of dichloromethane with 69 mg (0.6 mmol) of methanesulfonic acid chloride and 61 mg (0.6 mmol) of triethylamine and stirred together for 1.5 hours at room temperature. Then, it is washed once with dilute sodium bicarbonate solution, dried, filtered and concentrated by evaporation. The residue is chromatographed via flash chromatography (5 g of Isolute) with a gradient of cyclohexane:ethyl acetate=100:0 to 50:50 as an eluant. 80 mg (30% of theory) of 2-[(2-bismethanesulfonylamino-pyridin-4-ylmethyl)-amino]-N-(3-trifluoromethyl-phenyl)-benzamide is obtained as a resin.

(MS: m/e 542)

EXAMPLE 6.0

Production of 2-[(2-Butyrylamino-pyridin-4-ylmethyl)-amino]-N-(3-isoquinolinyl)-benzamide

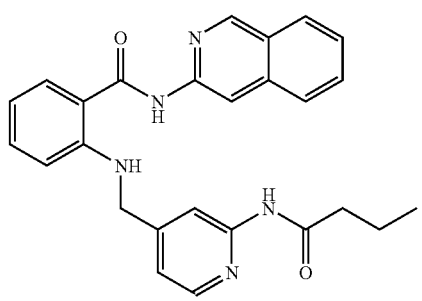

100 mg (0.23 mmol) of 2-[(2-bromopyridin-4-ylmethyl)-amino]-N-(3-isoquinolinyl)-benzamide is heated in 1 ml of dioxane with 89 mg (0.28 mmol) of cesium carbonate, 24 mg (0.69 mmol) of butyramide, 4.7 mg (0.0046 mmol) of dipalladium-tribenzylidene acetone and 7.9 mg (0.014 mmol) of Xanthphos under a cover gas and in a moisture-free environment for 25 hours to a bath temperature of 90° C. It is then mixed with 20 ml of methylene chloride, suctioned off and concentrated by evaporation. The residue is chromatographed on silica gel first with hexane, then with hexane:ethyl acetate=8:2 and then with hexane:ethyl acetate=1:1 as an eluant. 45 mg (42% of theory) of 2-[(2-butyrylamino-pyridin-4-ylmethyl)-amino]-N-(3-isoquinolinyl)-benzamide with a melting point of 173° C. is obtained.

Similarly produced are:

| Example No. | R¹ | R² | MW | Melting Point [° C.] or MS Molar Peak (m/e) |
|---|---|---|---|---|
| 6.1 | 3-CF₃-phenyl | —COn-Prop | 456.47 | 168 |
| 6.2 | isoquinolin-3-yl | —COMe | 411.46 | 220 |
| 6.3 | isoquinolin-3-yl | —COEt | 425.49 | 183 |
| 6.4 | isoquinolin-3-yl | —COn-Bu | 453.54 | 167 |
| 6.5 | isoquinolin-3-yl | —CO-cyclopropyl | 437.50 | 218 |
| 6.6 | isoquinolin-3-yl | —CO-(4-biphenyl) | 549.63 | 212 |
| 6.7 | isoquinolin-3-yl | —CO-isobutyl | 453.54 | 112 |
| 6.8 | isoquinolin-3-yl | —CO-(4-tert-butylphenyl) | 529.64 | 219 |

-continued

| Example No. | R¹ | R² | MW | Melting Point [° C.] or MS Molar Peak (m/e) |
|---|---|---|---|---|
| 6.9 | isoquinolin-3-yl | 1-naphthyl-CO- | 523.59 | 215 |
| 6.10 | isoquinolin-3-yl | —COt-Bu | 453.54 | 91 |
| 6.11 | 3-(CF₃)phenyl | 4-(t-Bu)phenyl-CO- | 546.59 | 111 |
| 6.12 | isoquinolin-3-yl | —COOEt | 441.50 | 185 |
| 6.13 | 3-(CF₃)phenyl | COMe | 428.41 | 185 |
| 6.14 | 1H-indazol-6-yl | CO-cycl.Prop | 426.48 | 210–212 |
| 6.15 | 1H-indazol-5-yl | CO-cycl.Prop | 426.48 | 127–128 |
| 6.16 | 3-(CF₃)phenyl | 3-(CF₃)phenyl-CO- | 558.48 | |
| 6.17 | 3-(CF₃)phenyl | COPh | 490.48 | |

-continued

| Example No. | R¹ | R² | MW | Melting Point [° C.] or MS Molar Peak (m/e) |
|---|---|---|---|---|
| 6.18 | 3-CF₃-phenyl | 3-F-phenyl-CO- | 508.47 | |
| 6.19 | 2-Me-2H-indazol-6-yl | CO-cycl.Prop | 440.51 | 114–115 |
| 6.20 | isoquinolin-3-yl | CO—(CH₂)₄—OH | 469.54 | 136 |
| 6.21 | 1-Me-1H-indazol-6-yl | —COOEt | 444.49 | 205–210 |
| 6.22 | 1H-indazol-6-yl | —COOEt | 430.47 | |
| 6.23 | 1-Me-1H-indazol-6-yl | CO₂CH₂(i-Prop) | 472.55 | 187 |
| 6.24 | 1-Me-1H-indazol-6-yl | CO₂(i-Prop) | 458.52 | 204 |
| 6.25 | 1-Me-1H-indazol-6-yl | CO-cycl.Prop | 440.51 | 105–107 |
| 6.26 | 3-CF₃-phenyl | pyridin-3-yl-CO- | 491.47 | |

-continued

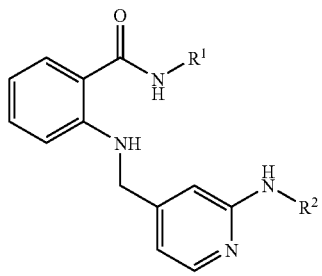

| Example No. | R¹ | R² | MW | Melting Point [° C.] or MS Molar Peak (m/e) |
|---|---|---|---|---|
| 6.27 | 1H-indazol-5-yl | COOEt | 430.47 | 213 |
| 6.28 | 2-methyl-2H-indazol-6-yl | COOEt | 444.49 | 194–196 |
| 6.29 | 3-CF₃-phenyl | CO-cycl-Prop | 545.45 | 213 |
| 6.30 | 3-CF₃-phenyl | CO-t-Bu | 470.49 | 155 |
| 6.31 | isoquinolin-3-yl | —CO—CH₂—O—(CH₂)₂OH | 471.51 | 86 |

EXAMPLE 6.32

Similarly produced is:

2-{[2-(Acetyl-methyl-amino)-pyridin-4-ylmethyl]-amino}-N-isoquinolin-3-yl-benzamide

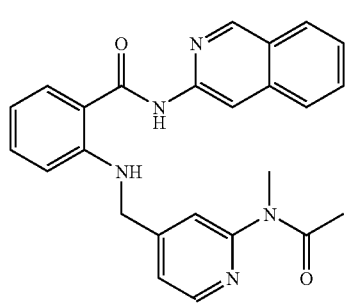

Melting point 71° C.

EXAMPLE 7.0

Production of 2-{[2-(2-Oxo-pyrrolidin-1-yl)-pyridin-4-ylmethyl]-amino}-N-(3-tribenzylidene

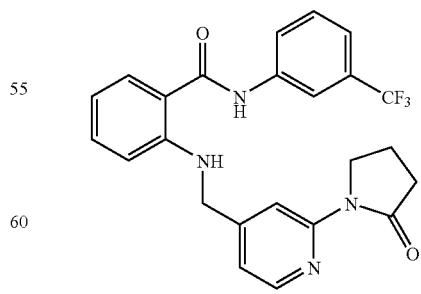

156 mg (0.5 mmol) of 2-{[2-(2-oxo-pyrrolidin-1-yl)-pyridin-4-ylmethyl]-amino}-benzoic acid is mixed in 5 ml of dimethylformamide with 0.12 ml (1 mmol) of 3-aminobenzotrifluoride, 228 mg (0.6 mmol) of HATU (N-dimethylamino-1H-1,2,3-triazolo-[4,5-b]pyridin-1-ylmethylene]-N-methylmethanammoniumhexafluorophosphate-N-oxide) and 0.14 ml of N-methylmorpholine, and it is stirred overnight at room temperature. It is diluted with ethyl acetate and washed in succession with saturated sodium bicarbonate solution, water and saturated common salt solution. The organic phase is dried, filtered and concentrated by evaporation. The residue is chromatographed on Isolute as a mobile solvent. 95 mg (42% of theory) of 2-{[2-(2-oxo-pyrrolidin-1-yl)-pyridin-4-ylmethyl]-amino}-N-(3-trifluoromethyl-phenyl)-benzamide is obtained.

(MS: m/e 454)

Similarly produced are:

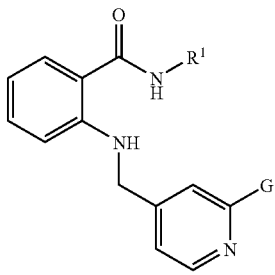

$R^2$, $R^3$, Y and Z = G

| Example No. | $R^1$ | G | MW | Melting Point [° C.] or MS Molar Peak (m/e) |
|---|---|---|---|---|
| 7.1 | isoquinoline | oxazolidinone | 439.5 | 189° C. |
| 7.2 | 3-CF3-phenyl | imidazolidinone-NH | 455.4 | m/e 455 |
| 7.3 | 3-CF3-phenyl | N-Me imidazolidinone | 469.5 | 209 |
| 7.4 | isoquinoline | imidazolidinone-NH | 438.5 | 154 |
| 7.5 | isoquinoline | pyrrolidinone | 435.5 | 217.3 |
| 7.6 | 1H-indazol-5-yl | pyrrolidinone | 426.48 | 195–200 |
| 7.7 | 1H-indazol-6-yl | pyrrolidinone | 426.48 | 105–110 |

EXAMPLE 8.0
Produced similarly to Example 6.0 is:
2-{[2-(2-Hydroxymethyl-5-oxo-pyrrolidin-1-yl)-pyridin-4-ylmethyl]-amino}-N-isoquinolin-3-yl-benzamide
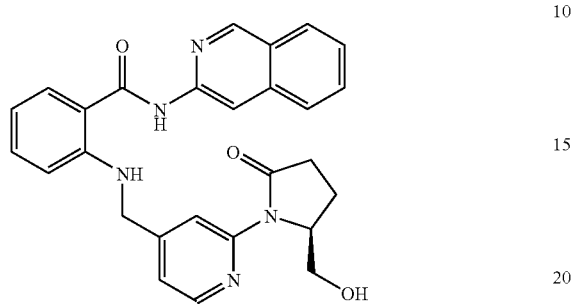
Similarly produced to this are:
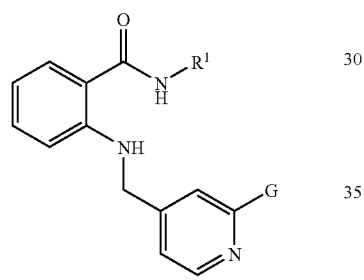
| Example No. | R¹ | G | MW | Melting Point [° C.] or MS Molar Peak (m/e) |
|---|---|---|---|---|
| 8.1 | 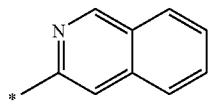 | 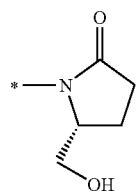 | 467.53 | 98° C. |
| 8.2 | 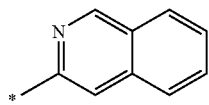 | 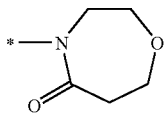 | 467.53 | 76° C. |
| 8.3 | 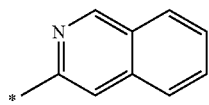 | 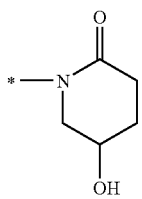 | 467.53 | 95° C. |

-continued

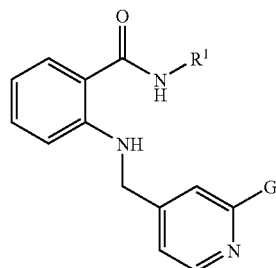

| Example No. | R¹ | G | MW | Melting Point [° C.] or MS Molar Peak (m/e) |
|---|---|---|---|---|
| 8.4 | isoquinolin-3-yl | 1-(2-oxo-pyridinyl) | 447.50 | 86° C. |
| 8.5 | isoquinolin-3-yl | 1-(5-chloro-2-oxo-pyridinyl) | 481.94 | 186° C. |
| 8.6 | 1-methyl-1H-indazol-6-yl | 1-(2-oxo-pyrrolidinyl) | 440.51 | 196–198 |
| 8.7 | 2-methyl-2H-indazol-6-yl | 1-(2-oxo-pyrrolidinyl) | 440.51 | 100 (Dec.) |
| 8.8 | 2-methyl-2H-indazol-5-yl | 1-(2-oxo-pyrrolidinyl) | 440.51 | 159 |
| 8.9 | 1-methyl-1H-indazol-5-yl | 1-(2-oxo-pyrrolidinyl) | 440.51 |  |
| 8.10 | 2-methyl-2H-indazol-6-yl | 1-(2-oxo-imidazolidinyl) | 441.49 |  |
| 8.11 | 2-methyl-2H-indazol-5-yl | 1-(2-oxo-imidazolidinyl) | 441.49 |  |

-continued
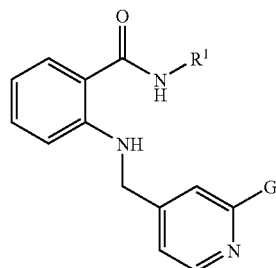
| Example No. | R¹ | G | MW | Melting Point [° C.] or MS Molar Peak (m/e) |
|---|---|---|---|---|
| 8.12 | 1-Me-1H-indazol-5-yl | 2-oxoimidazolidin-1-yl | 441.49 | |
| 8.13 | 1-Me-1H-indazol-6-yl | 2-oxoimidazolidin-1-yl | 441.49 | |
| 8.14 | 2-Me-2H-indazol-5-yl | 2-oxopiperidin-1-yl | 454.33 | |
| 8.15 | 1-Me-1H-indazol-6-yl | 2-oxopiperidin-1-yl | 454.33 | |
| 8.16 | 2-Me-2H-indazol-6-yl | 2-oxopiperidin-1-yl | 454.33 | |
| 8.17 | 1-Me-1H-indazol-5-yl | 2-oxopiperidin-1-yl | 454.33 | |
| 8.18 | 2-i-Prop-2H-indazol-5-yl | 2-oxopyrrolidin-1-yl | 468.56 | |
| 8.19 | 1-i-Prop-1H-indazol-5-yl | 2-oxopyrrolidin-1-yl | 468.56 | |

EXAMPLE 9.0

Production of 2-{[2-(2,5-Dioxo-pyrrolidin-1-yl)-pyridin-4-ylmethyl]-amino}-N-(3-trifluoromethyl-phenyl)-benzamide

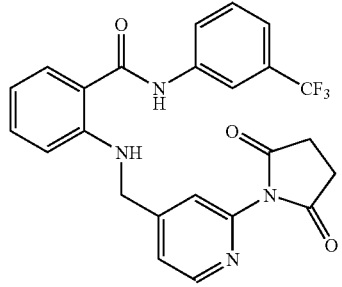

193 mg (0.5 mmol) of 2-[(2-amino-pyridin-4-ylmethyl)-amino]-N-(3-trifluoromethyl-phenyl)-benzamide is mixed in 20 ml of dichloromethane with 0.21 ml (1.5 mmol) of triethylamine, and it is mixed at room temperature drop by drop with a solution of 93 mg (0.6 mmol) of succinic acid dichloride in 3 ml of methylene chloride. After stirring overnight at room temperature, it is diluted with methylene chloride and washed in succession with water, saturated sodium bicarbonate solution and saturated common salt solution. Then, the organic phase is dried, filtered and concentrated by evaporation. The residue is chromatographed on Isolute (Separtis Company) with a gradient of methylene chloride:ethanol=100:0 to 95:5. 120 mg (51% of theory) of 2-{[2-(2,5-dioxo-pyrrolidin-1-yl)-pyridin-4-ylmethyl]-amino}-N-(3-trifluoromethyl-phenyl)-benzamide is obtained.

(MS: m/e 468)

Similarly produced is:

EXAMPLE 9.1

2-{[2-(3,5-Dioxo-morpholin-4-yl)-pyridin-4-ylmethyl]-amino}-N-(3-trifluoromethyl-phenyl)-benzamide

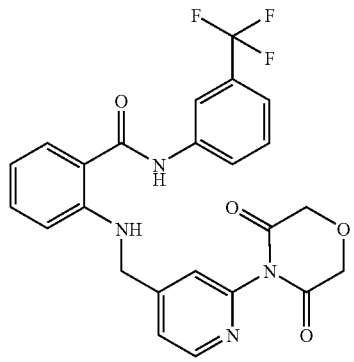

Melting point 201.9° C.

EXAMPLE 10.0

Production of 2-[(2-(3-Chloropropanesulfonylamino-pyridin-4-ylmethyl)-amino]-N-(3-trifluoromethyl-phenyl)-benzamide

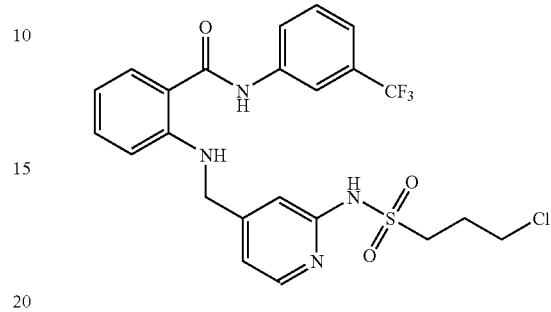

135 mg (0.35 mmol) of 2-[(2-amino-pyridin-4-ylmethyl)-amino]-N-(3-trifluoromethyl-phenyl)-benzamide is mixed in 10 ml of dichloromethane with 62 mg (0.35 mmol) of 3-chloropropanesulfonic acid chloride and 49 µl (0.35 mmol) of triethylamine, and it is stirred for 2 hours at room temperature. Then, it is washed once with saturated sodium bicarbonate solution, filtered and concentrated by evaporation. The residue is chromatographed via flash chromatography (5 g of Isolute) with a gradient of dichloromethane:ethanol=100:0 to 90:10 as an eluant. 67 mg (36% of theory) of 2-[(2-(3-chloropropanesulfonylamino-pyridin-4-ylmethyl)-amino]-N-(3-trifluoromethyl-phenyl)-benzamide is obtained.

(MS (CI): 491 (100%, M$^+$+H—HCl))

EXAMPLE 11.0

Production of 2-{[2-(1,1-Dioxo-1λ$^6$-isothiazolidin-2-yl)-pyridin-4-ylmethyl]-amino}-N-(3-trifluoromethyl-phenyl)-benzamide

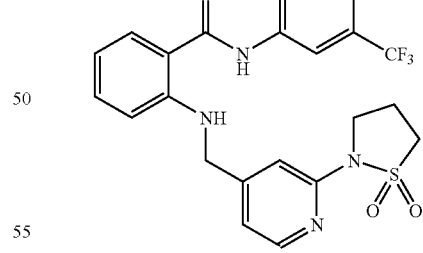

58 mg (0.11 mmol) of 2-[(2-(3-chloropropanesulfonylamino-pyridin-4-ylmethyl)-amino]-N-(3-trifluoromethyl-phenyl)-benzamide is suspended in 5 ml of ethanol and mixed with 5 mg of sodium hydride (55% in mineral oil). The mixture is refluxed for 1 hour, mixed with 10 ml of water and extracted with ethyl acetate. The aqueous phase is saturated with sodium sulfate and extracted repeatedly by stirring with ethyl acetate overnight. After the combined extracts are concentrated by evaporation, 50 mg (93% of theory) of 2-{[2-(1,1-dioxo-1λ$^6$-isothiazolidin-2-yl)-pyridin-4-ylmethyl]-amino}-N-(3-trifluoromethyl-phenyl)-benzamide is obtained.

(MS (CI): 491 (100%, M⁺+H))

EXAMPLE 12.0

N-[2-(2-Hydroxy-ethyl)-2H-indazol-5-yl]-2-{[2-(3-methyl-ureido)-pyridin-4-ylmethyl]-amino}-benzamide

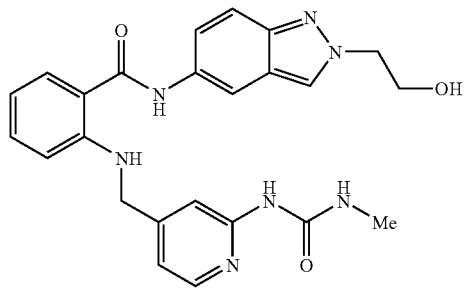

50 mg (0.11 mmol) of N-[2-(2-methoxy-ethyl)-2H-indazol-5-yl]-2-{[2-(3-methyl-ureido)-pyridin-4-ylmethyl]-amino}-benzamide is introduced into 5 ml of methylene chloride and mixed drop by drop under argon and in a moisture-free environment at −78° C. with 0.56 ml of boron tribromide (1 molar in methylene chloride). It is stirred for 15 more minutes, the cold bath is removed, and it then is stirred for 2 more hours. Then, it is mixed with water, the methylene chloride is drawn off, made alkaline with sodium bicarbonate solution and extracted twice with 15 ml each of ethyl acetate. The collected organic phase is dried, filtered, and concentrated by evaporation. The residue is chromatographed on silica gel with a gradient of methylene chloride: ethanol=100:0 to 90:10 as an eluant, and 27 mg of N-[2-(2-hydroxy-ethyl)-2H-indazol-5-yl]-2-{[2-(3-methyl-ureido)-pyridin-4-ylmethyl]-amino}-benzamide is obtained.

Similarly produced from the corresponding methoxy compounds are:

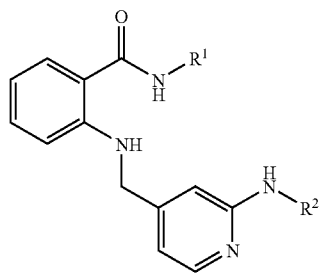

| Example No. | R¹ | R² | MW | Melting Point [° C.] or MS Molar Peak (m/e) |
|---|---|---|---|---|
| 12.1 | ![6-indazole N-Me] | ![acetamide ethanol] | 459.51 | 187 |
| 12.2 | ![6-indazole N-CH2CH2OH] | ![N-methyl acetamide] | 459.51 | 228 |
| 12.3 | ![6-indazole 2N-CH2CH2OH] | ![N-methyl acetamide] | 459.51 | 229 |
| 12.4 | ![5-indazole 1N-CH2CH2OH] | ![N-methyl acetamide] | 459.51 | |

-continued

| Example No. | R¹ | R² | MW | Melting Point [° C.] or MS Molar Peak (m/e) |
|---|---|---|---|---|
| 12.5 | 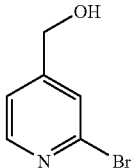 | 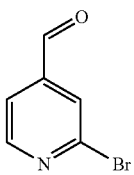 | 459.51 | 220 |

Production of Intermediate Compounds

EXAMPLE A

If the production of intermediate compounds is not described, the latter are known or can be produced analogously to known compounds or to processes that are described here.

Stage 1 a) Production of 2-Bromopyridine-5-carbaldehyde

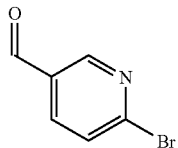

is carried out according to F. J. Romero-Salguerra et al. THL 40,859 (1999).

b) Production of 2-Bromo-isonicotinic Acid

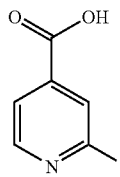

160 g (0.93 mol) of 2-bromo-4-methyl-pyridine is added in drops to 152 g (0.96 mol) of potassium permanganate in 4 l of water. Then, it is stirred under reflux for one hour before 152 g (0.96 mol) of potassium permanganate is added once more. After two additional hours of stirring under reflux, it is suctioned off in a hot state over Celite and washed with water. The aqueous phase is shaken out three times with dichloromethane. The aqueous phase is concentrated by evaporation to one-half its original volume, and the pH is set at 2 with concentrated hydrochloric acid. The precipitated solid is suctioned off and dried at 70° C. in a vacuum. 56.5 g of white solid product accumulates.

Production of 2-Bromo-4-hydroxymethyl-pyridine 30.2 ml (295 mmol) of triethylamine is added to 56.5 g (280 mmol) of 2-bromo-isonicotinic acid in 1.2 l of THF. Then, it is cooled to −10° C. and mixed drop by drop with 38.2 ml (295 mmol) of isobutyl chloroformate. After stirring has been continued for one hour at −10° C., it is cooled to −70° C. and mixed drop by drop with 590 ml (590 mmol) of LiAlH₄ solution (1 M in THF). After stirring is continued for one hour at −70° C., it is allowed to reach −40° C. 600 ml of 50% acetic acid is added. It is stirred overnight at room temperature. The insoluble components are suctioned off, and the filtrate is concentrated by evaporation. The residue is purified on silica gel with hexane and hexane/ethyl acetate 1:1. 28.0 g of white solidifying oil accumulates.

Production of 2-Bromo-4-formyl-pyridin 149 g (1714 mmol) of manganese dioxide is added in measured quantities to 28.0 g (148.9 mmol) of 2-bromo-4-hydroxymethyl-pyridine in 500 ml of dichlormethane within 6 hours. Then, stirring is continued at room temperature for 48 hours. It is suctioned off over Celite and concentrated by evaporation. 16.4 g of solidifying white oil accumulates.

2-Bromo-4-formyl-pyridine can also be produced according to THL 42, 6815 (2001) from 2-bromo-4-picoline in two stages.

Stage 2

Production of 2-[(6-Bromo-pyridin-3-ylmethyl)-amino]-N-isoquinolin-3-yl-benzamide

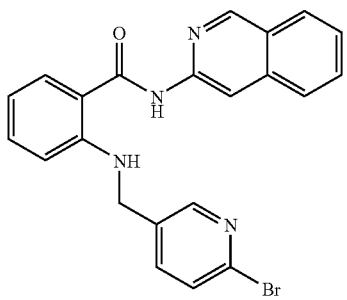

3.46 g (13.17 mmol) of 2-amino-N-isoquinolin-3-yl-benzamide is introduced into 50 ml of methanol, mixed with 1.5 ml of glacial acetic acid as well as 2.45 g (13.17 mmol) of 2-bromopyridine-5-carbaldehyde and stirred for 24 hours under argon and in a moisture-free environment at room temperature. Then, it is mixed with 828 mg (13.17 mmol) of sodium cyanoborohydride and stirred for another 24 hours at room temperature. After concentration by evaporation under vacuum, the residue is taken up in dilute sodium bicarbonate solution and suctioned off. The residue that is obtained is absorptively precipitated in a little ethyl acetate and suctioned off repeatedly. The residue that is obtained in this case is chromatographed on silica gel with hexane:ethyl acetate=1:1 as an eluant. 3.27 g (57% of theory) of 2-[(6-bromo-pyridin-3-ylmethyl)-amino]-N-isoquinolin-3-yl-benzamide is obtained.

Similarly produced are:

2-[(2-Bromo-pyridin-4-ylmethyl)-amino]-N-isoquinolin-3-yl-benzamide

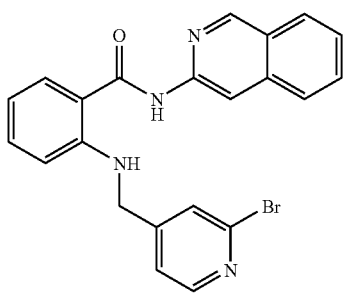

2-[(2-Bromo-pyridin-4-ylmethyl)-amino]-N-(3-trifluoromethyl-phenyl)-benzamide

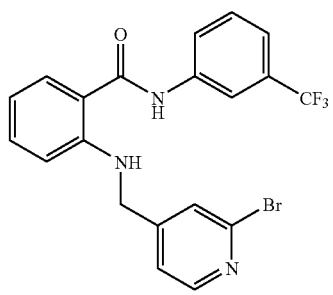

EXAMPLE B

1st Stage

Production of 2-[(2-Bromo-pyridin-4-ylmethyl)-amino]-benzoic Acid Methyl Ester

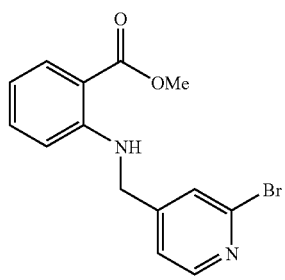

6.04 g (40 mmol) of anthranilic acid methyl ester in 600 ml of methanol is mixed with 3.2 ml of acetic acid and 7.4 g (40 mmol) of 2-bromopyridine-4-carbaldehyde and stirred overnight at 40° C. 3.8 g (60 mmol) of sodium cyanoborohydride is added thereto and stirred overnight at 40° C. 3.8 g (60 mmol) of sodium cyanoborohydride is added again and stirred over the weekend at 40° C. It is mixed with water and largely concentrated by evaporation. The aqueous phase is extracted with ethyl acetate, and the combined organic phases are dried, filtered and concentrated by evaporation. The crude product is chromatographed on silica gel with a gradient that consists of hexane and hexane/ethyl acetate 1:3 and hexane/ethyl acetate 1:1 as an eluant. 10.0 g (78% of theory) of 2-[(2-bromo-pyridin-4-ylmethyl)-amino]-benzoic acid methyl ester is obtained as a colorless oil.

EXAMPLE C

1st Stage

Production of 2-[(2-Bromo-pyridin-4-ylmethyl)-amino]-benzoic Acid

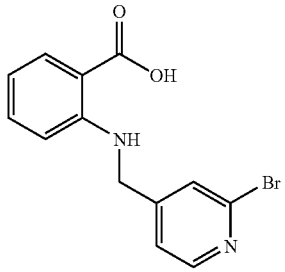

10.0 g (31.2 mmol) of 2-[(2-bromo-pyridin-4-ylmethyl)-amino]-benzoic acid methyl ester is dissolved in 290 ml of ethanol and mixed with 31.2 ml of 2 M sodium hydroxide solution. After having been stirred overnight at room temperature, the ethanol is drawn off, and the aqueous phase is shaken out with ethyl acetate. The aqueous phase is acidified with concentrated hydrochloric acid. The precipitate that is formed is suctioned off and dried. 5.93 g (62%) of 2-[(2-bromo-pyridin-4-ylmethyl)-amino]-benzoic acid accumulates in the form of a white solid.

2nd Stage

Production of 2-[(2-Bromo-pyridin-4-ylmethyl)-amino]-N-(2-methyl-2H-indazol-6-yl)-benzamide

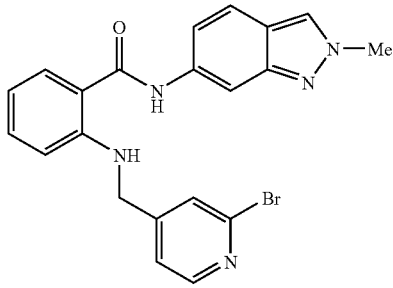

0.500 g (1.6 mmol) of 2-[(2-bromo-pyridin-4-ylmethyl)-amino]-benzoic acid, 0.471 g (3.2 mmol) of 2-methyl-2H-indazol-6-ylamine, 0.4 ml (3.68 mmol) of N-methylmorpholine and 0.729 g (1.92 mmol) of O-(7-azabenzotriazol-1-yl)-1,1,3,3-tetramethyluroniumhexafluorophosphate (HATU) in 25 ml of dimethylformamide are stirred for 16 hours at room temperature. The dimethylformamide is drawn off in an oil pump vacuum. The remaining residue is drawn off in saturated sodium bicarbonate solution. It is extracted three times with ethyl acetate, and the combined organic phases are dried, filtered and concentrated by evaporation. The residue is chromatographed on silica gel with a gradient that consists of hexane:acetone=100:0 to 50:50 as an eluant. 0.669 g (96% of theory) of 2-[(2-bromo-pyridin-4-ylmethyl)-amino]-N-(2-methyl-2H-indazol-6-yl)-benzamide is obtained in the form of a beige foam.

Similarly produced are also the following compounds:

2-[(2-Bromo-pyridin-4-ylmethyl)-amino]-N-(1-methyl-1H-indazol-6-yl)-benzamide

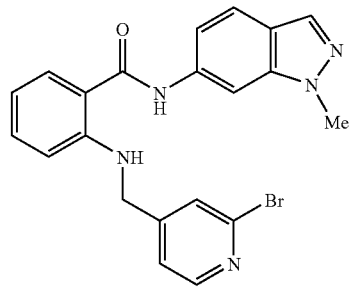

2-[(2-Bromo-pyridin-4-ylmethyl)-amino]-N-(1H-indazol-6-yl)-benzamide

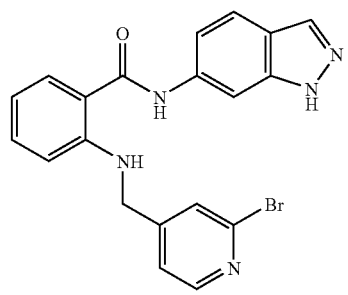

2-[(2-Bromo-pyridin-4-ylmethyl)-amino]-N-(1H-indazol-5-yl)-benzamide

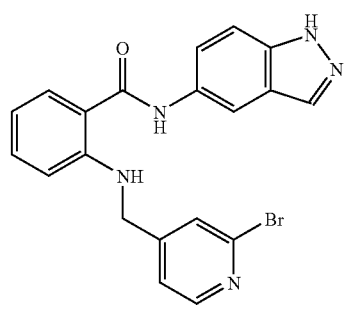

EXAMPLE D

Stage 1

Production of 2-{[2-(2-Oxo-pyrrolidin-1-yl)-pyridin-4-ylmethyl]-amino}-benzoic Acid Methyl Ester

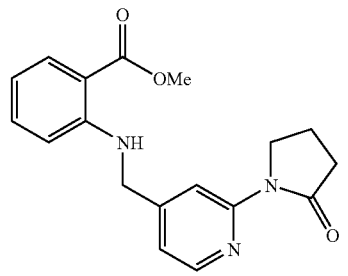

870 mg (2.78 mmol) of 2-[(2-bromo-pyridin-4-ylmethyl)-amino]-benzoic acid methyl ester, 53 mg (0.28 mmol) of copper (I) iodide, 1.126 g (5.5 mmol) of potassium phosphate and 0.26 ml (3.6 mmol) of pyrrolidin-2-one are refluxed in 15 ml of dioxane for 8 hours. After water is added, the dioxane is distilled off in a vacuum, made alkaline with about 12% ammonia solution and shaken out several times with ethyl acetate. The collected ethyl acetate phase is washed, dried, filtered and concentrated by evaporation. As a residue, 700 mg (77% of theory) of 2-{[2-(2-oxo-pyrrolidin-1-yl)-pyridin-4-ylmethyl]-amino}-benzoic acid methyl ester is obtained as a crude product, which is used without further purification in the next stage.

Similarly produced are:

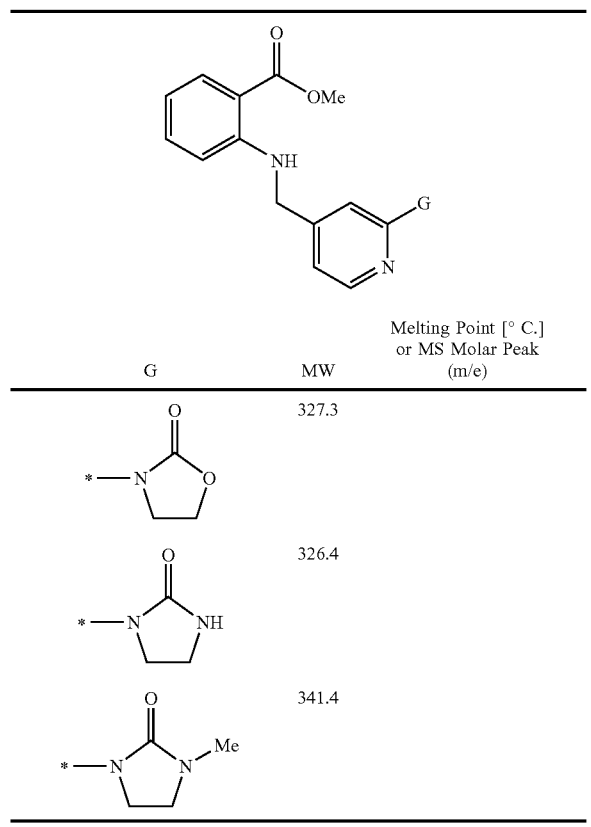

| G | MW | Melting Point [° C.] or MS Molar Peak (m/e) |
|---|---|---|
| (oxazolidinone) | | 327.3 |
| (imidazolidinone NH) | | 326.4 |
| (imidazolidinone NMe) | | 341.4 |

Stage 3

Production of 2-{[2-(2-Oxo-pyrrolidin-1-yl)-pyridin-4-ylmethyl]-amino}-benzoic Acid

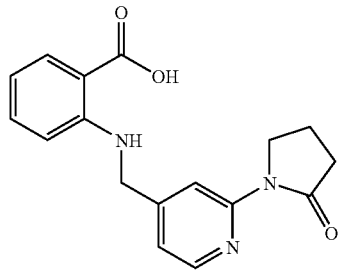

700 mg (2.15 mmol) of 2-{[2-(2-oxo-pyrrolidin-1-yl)-pyridin-4-ylmethyl]-amino}-benzoic acid methyl ester is mixed in 15 ml of methanol with 2.7 ml of 1N sodium hydroxide solution and refluxed for 1 hour. After the methanol is distilled off in a vacuum, it is diluted with water and shaken once with ethyl acetate. The aqueous phase is mixed with 5 ml of 1 mol citric acid solution and stirred overnight. The solid precipitation is suctioned off and very quickly dried. 600 mg of 2-{[2-(2-oxo-pyrrolidin-1-yl)-pyridin-4-ylmethyl]-amino}-benzoic acid, which is used as a crude product in the next stage, is obtained.

Similarly produced are:

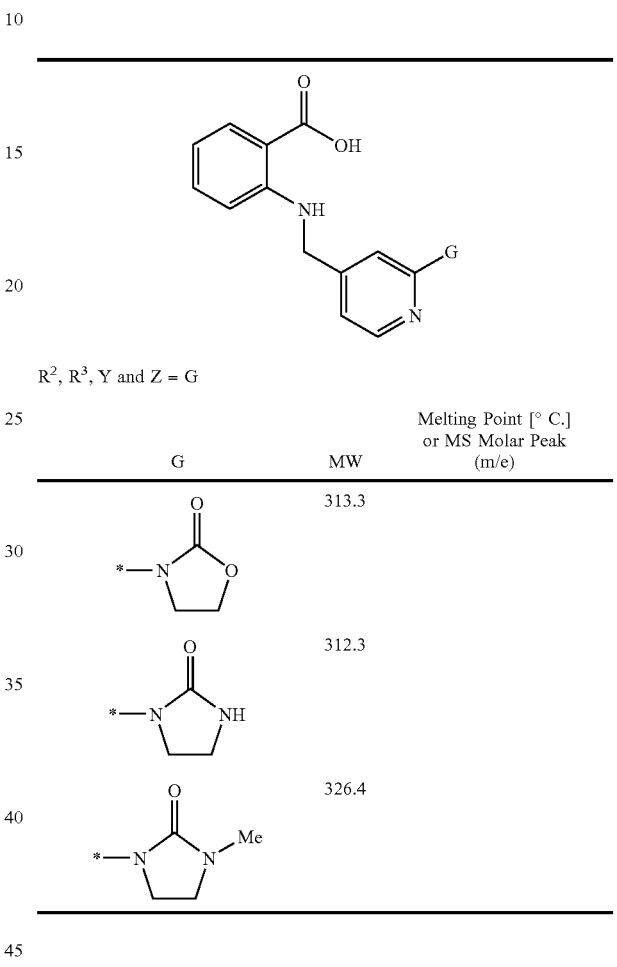

$R^2$, $R^3$, Y and Z = G

| G | MW | Melting Point [° C.] or MS Molar Peak (m/e) |
|---|---|---|
| (oxazolidinone) | | 313.3 |
| (imidazolidinone NH) | | 312.3 |
| (imidazolidinone NMe) | | 326.4 |

EXAMPLE E

Production of 2-[(2-Bromo-pyridin-4-ylmethyl)-amino]-N-(1-methyl-1H-indazol-5-yl)-benzamide and 2-[(2-Bromo-pyridin-4-ylmethyl)-amino]-N-(2-methyl-2H-indazol-5-yl)-benzamide

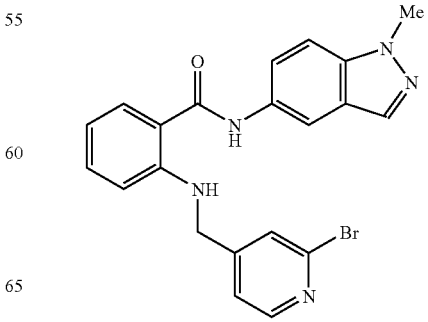

-continued

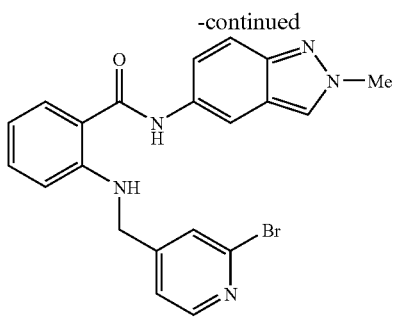

4.22 g (10 mmol) of 2-[(2-bromo-pyridin-4-ylmethyl)-amino]-N-(1H-indazol-5-yl)-benzamide is mixed in 30 ml of dimethylformamide while being cooled with ice with 3.6 g (11 mmol) of cesium carbonate and 0.68 ml (11 mmol) of methyl iodide, and it is stirred overnight at room temperature. It is then stirred into 250 ml of ice-cold water, stirring is continued for 15 minutes, and it is suctioned off. The filter cake is very quickly dried and chromatographed on silica gel with a gradient of ethyl acetate:hexane 1:1 to 100:0 as an eluant. 1.79 g (41% of theory) of 2-[(2-bromo-pyridin-4-ylmethyl)-amino]-N-(1-methyl-1H-indazol-5-yl)-benzamide with a melting point of 173.8° C. as well as 830 mg (19% of theory) of 2-[(2-bromo-pyridin-4-ylmethyl)-amino]-N-(2-methyl-2H-indazol-5-yl)-benzamide with a melting point of 183.8° C. are obtained.

Similarly produced are:
2-[(2-Bromo-pyridin-4-ylmethyl)-amino]-N-(1-isopropyl-1H-indazol-5-yl)-benzamide,
2-[(2-Bromo-pyridin-4-ylmethyl)-amino]-N-(2-isopropyl-2H-indazol-5-yl)-benzamide,
2-[(2-Bromo-pyridin-4-ylmethyl)-amino]-N-(1-ethyl-1H-indazol-5-yl)-benzamide,
2-[(2-Bromo-pyridin-4-ylmethyl)-amino]-N-(2-ethyl-2H-indazol-5-yl)-benzamide,
2-[(2-Bromo-pyridin-4-ylmethyl)-amino]-N-(1-[2-methoxyethyl]-1H-indazol-5-yl)-benzamide,
2-[(2-Bromo-pyridin-4-ylmethyl)-amino]-N-(2-[2-methoxyethyl]-2H-indazol-5-yl)-benzamide,
2-[(2-Bromo-pyridin-4-ylmethyl)-amino]-N-(1-[cyanomethyl]-1H-indazol-5-yl)-benzamide,
2-[(2-Bromo-pyridin-4-ylmethyl)-amino]-N-(2-[cyanomethyl]-2H-indazol-5-yl)-benzamide,
2-[(2-Bromo-pyridin-4-ylmethyl)-amino]-N-(1-[2-dimethylaminoethyl]-1H-indazol-5-yl)-benzamide,
2-[(2-Bromo-pyridin-4-ylmethyl)-amino]-N-(2-[2-dimethylaminoethyl]-2H-indazol-5-yl)-benzamide,
2-[(2-Bromo-pyridin-4-ylmethyl)-amino]-N-(1-methyl-1H-indazol-6-yl)-benzamide,
2-[(2-Bromo-pyridin-4-ylmethyl)-amino]-N-(2-methyl-2H-indazol-6-yl)-benzamide,
2-[(2-Bromo-pyridin-4-ylmethyl)-amino]-N-(1-isopropyl-1H-indazol-6-yl)-benzamide,
2-[(2-Bromo-pyridin-4-ylmethyl)-amino]-N-(2-isopropyl-2H-indazol-6-yl)-benzamide,
2-[(2-Bromo-pyridin-4-ylmethyl)-amino]-N-(1-ethyl-1H-indazol-6-yl)-benzamide,
2-[(2-Bromo-pyridin-4-ylmethyl)-amino]-N-(2-ethyl-2H-indazol-6-yl)-benzamide,
2-[(2-Bromo-pyridin-4-ylmethyl)-amino]-N-(1-[2-methoxyethyl]-1H-indazol-6-yl)-benzamide,
2-[(2-Bromo-pyridin-4-ylmethyl)-amino]-N-(2-[2-methoxyethyl]-2H-indazol-6-yl)-benzamide,
2-[(2-Bromo-pyridin-4-ylmethyl)-amino]-N-(1-[cyanomethyl]-1H-indazol-6-yl)-benzamide and
2-[(2-Bromo-pyridin-4-ylmethyl)-amino]-N-(2-[cyanomethyl]-2H-indazol-6-yl)-benzamide.
2-[(2-Bromo-pyridin-4-ylmethyl)-amino]-N-(1-[2-dimethylaminoethyl]-1H-indazol-6-yl)-benzamide and
2-[(2-Bromo-pyridin-4-ylmethyl)-amino]-N-(2-[2-dimethylaminoethyl]-2H-indazol-6-yl)-benzamide.

The sample applications below explain the biological action and the use of the compounds according to the invention without the latter being limited to the examples.

Solutions Required for the Tests

Stock solutions

Stock solution A: 3 mmol of ATP in water, pH 7.0 (−70° C.)

Stock solution B: g-33P-ATP 1 mCi/100 µl

Stock solution C: poly-(Glu4Tyr) 10 mg/mi in water

Solution for dilutions

Substrate solvent: 10 mmol of DTT, 10 mmol of manganese chloride, 100 mmol of magnesium chloride Enzyme solution: 120 mmol of tris/HCl, pH 7.5, 10 µM of sodium vanadium oxide Sample Application 1

Inhibition of the KDR- and FLT-1 Kinase Activity in the Presence of the Compounds According to the Invention In a microtiter plate (without protein binding) that tapers to a point, 10 µl of substrate mix (10 µl of volume of ATP stock solution A+25 µCi of g-33P-ATP (about 2.5 µl of stock solution B) +30 µl of poly-(Glu4Tyr) stock solution C+1.21 ml of substrate solvent), 10 µl of inhibitor solution (substances corresponding to the dilutions, 3% DMSO in substrate solvent as a control) and 10 µl of enzyme solution (11.25 µg of enzyme stock solution (KDR or FLT-1 kinase) are added at 4° C. in 1.25 ml of enzyme solution (dilute). It is thoroughly mixed and incubated for 10 minutes at room temperature. Then, 10 µl of stop solution (250 mmol of EDTA, pH 7.0) is added, mixed, and 10 µl of the solution is transferred to a P 81 phosphocellulose filter. Then, it is washed several times in 0.1 M phosphoric acid. The filter paper is dried, coated with Meltilex and measured in a microbeta counter.

The IC50 values are determined from the inhibitor concentration, which is necessary to inhibit the phosphate incorporation to 50% of the uninhibited incorporation after removal of the blank reading (EDTA-stopped reaction).

The results of the kinase inhibition IC50 in µM are presented in the table below.

Sample Application 2

Cytochrome P450 Inhibition

The Cytochrome P450 inhibition was performed according to the publication of Crespi et al. (Anal. Biochem., 248, 188–190 (1997)) with use of the baculovirus/insect cell-expressed, human Cytochrome P 450 isoenzyme (3A4).

The results are presented in the following table.

| Example No. | VEGFR II (KDR) [nM] | Cytochrome P450 Isoenzyme 3A4 μM |
|---|---|---|
| 2.54 from WO 00/27819 | 5 | 3.6 |
| 38 from WO 00/27820 | 180 | 4.6 |
| 1.14 | 52 | >30 |
| 3.24 | 12 | 14 |
| 3.30 | 10 | 5.5 |
| 6.2 | 41 | >30 |
| 6.22 | 24 | 10 |
| 6.27 | 8 | 10 |
| 6.32 | 65 | 11 |

The superior action of the compounds according to the invention compared to the known compounds can be seen clearly from the result.

What is claimed is:

1. A compound of formula I

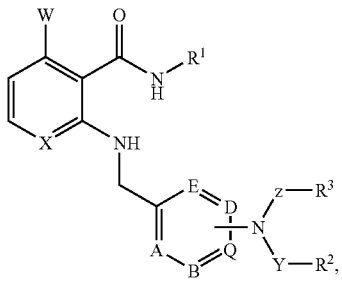

(I)

in which

X stands for CH,

W stands for hydrogen or fluorine,

A, B, D, and E each stand for a carbon atom, and Q, stands fo a nitrogen atom, $R^1$ stands for indazolyl, which is optionally substituted in one or more places in the same way or differently with halogen, hydroxy, $C_1$–$C_{12}$-alkyl, $C_3$–$C_6$-cycloalkyl, $C_3$–$C_6$-alkenyl, $C_2$–$C_6$-alkinyl, aralkyloxy, $C_1$–$C_{12}$-alkoxy, halo-$C_1$–$C_6$-alkyl, cyano-$C_1$–$C_6$-alkyl or with the group =O, —$SO_2R^6$ or —$OR^5$, whereby the $C_1$–$C_6$-alkyl optionally also can be substituted with the group —$OR^5$ or —$NR^9R^{10}$, Y and Z, in each case independently of one another, stand for a bond or for the group =CO, =CS or =$SO_2$, $R^2$ and $R^3$, independently of one another, stand for hydrogen or for the group —$CONR^9R^{10}$, —$SO^2R^6$, —$COR^{11}$, —$COC_1$–$C_6$-alkyl, —CO—$C_1$–$C_6$-alkyl-$R^{11}$, —$NR^9R^{10}$ or for $C_1$–$C_6$-alkyl, $C_3$–$C_{10}$-cycloalkyl, $C_3$–$C_6$-cycloalkenyl, or aryl that is optionally substituted in one or more places in the same way or differently with halogen, cyano, $C_1$–$C_{12}$-alkyl, $C_1$–$C_{12}$-alkoxy, hydroxy-$C_1$–$C_6$-alkyl, halo-$C_1$–$C_6$-alkyl or with the group —$NR^7R^8$, —$OR^5$, —$C_1$–$C_6$-alkyl-$OR^5$, —$SR^4$, —$SOR^4$ or —$SO_2R^6$, $R^4$ stands for $C_1$–$C_{12}$-alkyl, or aryl, $R^5$ stands for hydrogen, $C_1$–$C_{12}$-alkyl, $C_3$–$C_{10}$-cycloalkyl, $C_1$–$C_{12}$-alkoxy, halo-$C_1$–$C_{12}$-alkyl, or halo-$C_3$–$C_6$-cycloalkyl, $R^6$ stands for hydrogen, $C_1$–$C_{12}$-alkyl, halo-$C_1$–$C_6$-alkyl, or aryl, or for the group —$NR^9R^{10}$, whereby the aryl is optionally substituted in one or more places in the same way or differently with $C_1$–$C_{12}$-alkyl, $C_1$–$C_6$-alkoxy, halogen or halo-$C_1$–$C_6$-alkoxy, $R^7$ and $R^8$, independently of one another, stand for hydrogen or $C_1$–$C_{12}$-alkyl, $R^9$ and $R^{10}$, independently of one another, stand for hydrogen, $C_1$–$C_6$-alkyl, $C_2$–$C_6$-alkenyl, aryl, $C_3$–$C_8$-cycloalkyl or for the group —$CONR^7R^8$, or for $C_1$–$C_{12}$-alkyl that is optionally substituted in one or more places in the same way or differently with aryl, hydroxy, halogen, $C_1$–$C_{12}$-alkoxy, or for the group —$NR^7R^8$, whereby the aryl optionally substituted in one or more places in the same way or differently with $C_1$–$C_6$-alkoxy or halo-$C_1$–$C_6$-alkyl, and $R^{11}$ stands for $C_1$–$C_6$-alkyl, $C_1$–$C_6$-alkoxy, hydroxy-$C_1$–$C_6$-alkyl, hydroxy-$C_1$–$C_6$-alkoxy, $C_3$–$C_6$-cycloalkyl, phenyl, biphenyl or naphthyl, whereby the phenyl is optionally substituted in one or more places in the same way or differently with $C_1$–$C_6$-alkyl, or halo-$C_1$–$C_6$-alkyl, or an isomer, diastereomer, tautomers or salt thereof.

2. A compound of formula I, according to claim 1, in which

W stands for hydrogen,

A, B, D, E and Q as a ring together stand for pyridyl,

Y and Z, in each case independently of one another, stand for a bond, $R^4$ stands for $C_1$–$C_6$-alkyl, or aryl, $R^5$ stands for hydrogen, $C_1$–$C_6$-alkyl, halo-$C_1$–$C_6$-alkyl, $C_1$–$C_{12}$-alkoxy, $C_3$–$C_{10}$-cycloalkyl or halo-$C_3$–$C_6$-cycloalkyl, $R^6$ stands for hydrogen, $C_1$–$C_6$-alkyl, halo-$C_1$–$C_6$-alkyl, or aryl, or for the group —$NR^9R^{10}$, whereby the aryl is optionally substituted in one or more places in the same way or differently with $C_1$–$C_6$-alkyl, $C_1$–$C_6$-alkoxy, halogen or halo-$C_1$–$C_6$-alkoxy, and $R^7$ and $R^8$, independently of one another, stand for hydrogen or $C_1$–$C_6$-alkyl, or an isomer, diastereomer, tautomer and salt thereof.

3. A compound of formula I, according to claims 1, in which

W stands for hydrogen,

A, B, D, E, and Q as a ring together stand for pyridyl, $R^1$ stands for indazolyl, which is optionally substituted in one or more places in the same way or differently with halogen, hydroxy, $C_1$–$C_6$-alkyl, $C_2$–$C_6$-alkinyl, $C_1$–$C_6$-alkoxy, halo-$C_1$–$C_6$-alkyl, or cyano-$C_1$–$C_6$-alkyl, whereby $C_1$–$C_6$-alkyl optionally also can be substituted with the group —$OR^5$ or —$NR^9R^{10}$, Y and Z, in each case independently of one another, stand for a bond, or for the group =CO, $R^2$ and $R^3$, independently of one another, stand for hydrogen or for the group —$CONR^9R^{10}$, —$SO_2R^6$, —$COR^{11}$, —$COC_1$–$C_6$-alkyl, —CO—$C_1$–$C_6$-alkyl-$R^{11}$, —$NR^9R^{10}$ or for $C_1$–$C_6$-alkyl or phenyl that is optionally substituted in one or more places in the same way or differently with the group —$NR^7R^8$ or —$OR^5$, $R^5$ stands for hydrogen or $C_1$–$C_6$-alkyl, $R^6$ stands for hydrogen, $C_1$–$C_6$-alkyl, halo-$C_1$–$C_6$-alkyl, phenyl, or benzyl, whereby the phenyl, or benzyl, are optionally substituted in one or more places in the same way or differently with $C_1$–$C_6$-alkyl, $C_1$–$C_6$-alkoxy, halogen or halo-$C_1$–$C_6$-alkoxy, $R^7$ and $R^8$, independently of one another, stand for hydrogen or $C_1$–$C_6$-alkyl, and $R^9$ and $R^{10}$, independently of one another, stand for hydrogen, $C_1$–$C_6$-alkyl, $C_2$–$C_6$-alkenyl, phenyl, biphenyl, $C_3$–$C_8$-cycloalkyl, naphthyl or for the group —CONR$^7$R$^8$ or for $C_1$–$C_6$-alkyl that is optionally substituted in one or more places in the same way or differently with phenyl, hydroxy, halogen, $C_1$–$C_{12}$-alkoxy, or with the group —NR$^7$R$^8$, whereby the phenyl is optionally substituted in one or more places in the same way or differently with $C_1$–$C_6$-alkoxy or halo-$C_1$–$C_6$-alkyl, or an isomer, diastereomer, tautomer or salt thereof.

\* \* \* \* \*

UNITED STATES PATENT AND TRADEMARK OFFICE
CERTIFICATE OF CORRECTION

PATENT NO. : 7,148,357 B2
APPLICATION NO. : 10/631018
DATED : December 12, 2006
INVENTOR(S) : Adreas Huth It is certified that error appears in the above-identified patent and that said Letters Patent is hereby corrected as shown below:

On the Title Page, Item (75) line 3, reads "Stuart" should read -- Stuart --
Column 73, line 43, reads "fo a" should read -- for a --
Column 74, line 14, reads "the aryl optionally" should read --the aryl is optionally --
Column 74, line 23, begin a new line before "or an isomer,"
Column 74, line 41, begin a new line before "or an isomer,"
Column 74, line 43, reads "claims 1," should read -- claim 1, --
Column 76, line 5, begin a new line before "or an isomer,"

Signed and Sealed this

Twenty-ninth Day of May, 2007

JON W. DUDAS
*Director of the United States Patent and Trademark Office*